United States Patent
Inhaber et al.

(10) Patent No.: US 10,898,631 B2
(45) Date of Patent: *Jan. 26, 2021

(54) DIRECT SODIUM REMOVAL METHOD, SOLUTION AND APPARATUS TO REDUCE FLUID OVERLOAD IN HEART FAILURE PATIENTS

(71) Applicant: Sequana Medical NV, Zwijnaarde (BE)

(72) Inventors: Neil Inhaber, Westborough, MA (US); Noel Johnson, Malvern, PA (US); Dirk Fengels, Ballwil (CH); Ian Crosbie, London (GB)

(73) Assignee: Sequana Medical NV, Zwijnaarde (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/985,617

(22) Filed: May 21, 2018

(65) Prior Publication Data

US 2018/0344917 A1    Dec. 6, 2018

Related U.S. Application Data

(60) Provisional application No. 62/510,652, filed on May 24, 2017.

(51) Int. Cl.
| | |
|---|---|
| *A61M 1/28* | (2006.01) |
| *A61P 7/08* | (2006.01) |
| *A61K 33/14* | (2006.01) |
| *A61K 9/00* | (2006.01) |
| *A61K 9/08* | (2006.01) |
| *A61K 31/7004* | (2006.01) |
| *A61K 31/716* | (2006.01) |
| *A61M 27/00* | (2006.01) |
| *A61M 31/00* | (2006.01) |
| *A61L 2/00* | (2006.01) |

(52) U.S. Cl.
CPC .......... *A61M 1/282* (2014.02); *A61K 9/0019* (2013.01); *A61K 9/08* (2013.01); *A61K 31/7004* (2013.01); *A61K 31/716* (2013.01); *A61K 33/14* (2013.01); *A61M 1/28* (2013.01); *A61M 1/285* (2013.01); *A61M 1/287* (2013.01); *A61M 27/002* (2013.01); *A61M 31/002* (2013.01); *A61P 7/08* (2018.01); *A61L 2/0047* (2013.01); *A61L 2202/21* (2013.01); *A61M 2205/18* (2013.01); *A61M 2205/3317* (2013.01); *A61M 2205/3337* (2013.01); *A61M 2205/3344* (2013.01); *A61M 2205/3368* (2013.01); *A61M 2205/3379* (2013.01); *A61M 2205/3569* (2013.01); *A61M 2205/3576* (2013.01); *A61M 2205/502* (2013.01); *A61M 2205/52* (2013.01); *A61M 2205/587* (2013.01); *A61M 2205/6009* (2013.01); *A61M 2205/70* (2013.01); *A61M 2205/8206* (2013.01); *A61M 2205/8243* (2013.01); *A61M 2209/086* (2013.01); *A61M 2209/088* (2013.01); *A61M 2210/1017* (2013.01); *A61M 2210/1085* (2013.01)

(58) Field of Classification Search
None
See application file for complete search history.

(56) References Cited

U.S. PATENT DOCUMENTS

| | | |
|---|---|---|
| 3,540,451 A | 11/1970 | Zenman |
| 3,575,158 A | 4/1971 | Summers |
| 3,654,932 A | 4/1972 | Newkirk et al. |
| 3,810,259 A | 5/1974 | Summers |
| 3,910,283 A | 10/1975 | Leveen |
| 4,014,346 A | 3/1977 | Brownlee et al. |
| 4,083,786 A | 4/1978 | Tsuda et al. |
| 4,240,434 A | 12/1980 | Newkirk |
| 4,261,341 A | 4/1981 | Hakim et al. |
| 4,354,933 A | 10/1982 | Lester |
| 4,416,657 A | 11/1983 | Berglund |
| 4,419,094 A | 12/1983 | Patel |
| 4,475,898 A | 10/1984 | Brodner et al. |
| 4,475,899 A | 10/1984 | Muller |
| 4,490,137 A | 12/1984 | Moukheibir |
| 4,553,956 A | 11/1985 | Muller |

(Continued)

FOREIGN PATENT DOCUMENTS

| | | |
|---|---|---|
| CN | 101485683 A | 7/2009 |
| CN | 201930383 U | 8/2011 |

(Continued)

OTHER PUBLICATIONS

François, et al., Peritoneal Dialysis for Chronic Congestive Heart Failure, Blood Purif., 40(1):45-52 (2015).

(Continued)

*Primary Examiner* — Robert A Wax
*Assistant Examiner* — Randeep Singh
(74) *Attorney, Agent, or Firm* — Eversheds Sutherland (US) LLP; Christopher C. Bolten; Nicola A. Pisano

(57) ABSTRACT

A Direct Sodium Removal method, apparatus and solution for treating patients in heart failure, and having a glomerular filtration rate greater than 15 mL/min/1.73 $m^2$, or residual kidney function corresponding to normal to CKD Stage 4, is provided in which a no or low sodium DSR infusate is administered to the peritoneal cavity for a predetermined dwell period and then removed, thereby removing sodium from the body. The resulting elimination of fluid from the patient by i) functioning of the kidneys through urination and ii) direct removal of osmotic ultrafiltrate from the peritoneal cavity, restores serum sodium concentrations to healthy levels and thereby reduces fluid overload in the patient.

21 Claims, 16 Drawing Sheets

(56) References Cited

U.S. PATENT DOCUMENTS

| | | |
|---|---|---|
| 4,610,625 A | 9/1986 | Bunn |
| 4,610,658 A | 9/1986 | Buchwald et al. |
| 4,615,691 A | 10/1986 | Hakim et al. |
| 4,618,343 A | 10/1986 | Polaschegg |
| 4,632,435 A | 12/1986 | Polyak |
| 4,657,530 A | 4/1987 | Buchwald et al. |
| 4,687,471 A | 8/1987 | Twardowski et al. |
| 4,725,207 A | 2/1988 | Buchwald et al. |
| 4,772,257 A | 9/1988 | Hakim et al. |
| 4,779,614 A | 10/1988 | Moise |
| 4,784,638 A | 11/1988 | Ghajar et al. |
| 4,850,955 A | 7/1989 | Newkirk et al. |
| 4,880,414 A | 11/1989 | Whipple |
| 4,904,236 A | 2/1990 | Redmont et al. |
| 4,963,129 A | 10/1990 | Rusch |
| 4,963,133 A | 10/1990 | Whipple |
| 5,011,472 A | 4/1991 | Aebischer et al. |
| 5,021,048 A | 6/1991 | Buckholtz |
| 5,037,385 A | 8/1991 | O'Byrne |
| 5,057,075 A | 10/1991 | Moncrief et al. |
| 5,071,408 A | 12/1991 | Ahmed et al. |
| 5,078,688 A | 1/1992 | Lobodzinski et al. |
| 5,147,281 A | 9/1992 | Thornton et al. |
| 5,167,615 A | 12/1992 | East et al. |
| 5,180,387 A | 1/1993 | Ghajar et al. |
| 5,254,084 A | 10/1993 | Geary |
| 5,356,386 A | 10/1994 | Goldberg et al. |
| 5,385,541 A | 1/1995 | Kirsch et al. |
| 5,387,188 A | 2/1995 | Watson |
| 5,387,192 A | 2/1995 | Glantz et al. |
| 5,391,143 A | 2/1995 | Kensey |
| 5,395,350 A | 3/1995 | Summers |
| 5,397,354 A | 3/1995 | Wilk et al. |
| 5,472,323 A | 12/1995 | Hirabayashi et al. |
| 5,474,683 A | 12/1995 | Bryant et al. |
| 5,575,770 A | 11/1996 | Melsky et al. |
| 5,589,197 A | 12/1996 | Shockley et al. |
| 5,629,025 A | 5/1997 | Shockley et al. |
| 5,631,025 A | 5/1997 | Shockley et al. |
| 5,637,083 A | 6/1997 | Bertrand et al. |
| 5,725,506 A | 3/1998 | Freeman et al. |
| 5,830,172 A | 11/1998 | Leveen et al. |
| 5,902,336 A | 5/1999 | Mishkin |
| 5,944,684 A | 8/1999 | Roberts et al. |
| 5,947,911 A | 9/1999 | Wong et al. |
| 5,980,478 A | 11/1999 | Gorsuch et al. |
| 5,989,207 A | 11/1999 | Hughes |
| 6,007,511 A | 12/1999 | Prywes |
| 6,017,355 A | 1/2000 | Hessel et al. |
| D420,738 S | 2/2000 | Carter et al. |
| 6,022,333 A | 2/2000 | Kensey |
| 6,132,405 A | 10/2000 | Nilsson et al. |
| 6,132,415 A | 10/2000 | Finch et al. |
| 6,162,238 A | 12/2000 | Kaplan et al. |
| 6,162,487 A | 12/2000 | Darouiche |
| 6,193,684 B1 | 2/2001 | Burbank et al. |
| 6,214,802 B1 | 4/2001 | Nakamura et al. |
| 6,245,039 B1 | 6/2001 | Brugger et al. |
| 6,248,726 B1 | 6/2001 | Alsop et al. |
| 6,254,567 B1 | 7/2001 | Treu et al. |
| 6,264,601 B1 | 7/2001 | Jassawalla et al. |
| 6,264,625 B1 | 7/2001 | Rubenstein et al. |
| 6,417,750 B1 | 7/2002 | Sohn |
| 6,436,087 B1 | 8/2002 | Lewis et al. |
| 6,533,733 B1 | 3/2003 | Ericson et al. |
| 6,554,822 B1 | 4/2003 | Holschneider et al. |
| 6,585,681 B2 | 7/2003 | Brugger et al. |
| 6,613,095 B1 | 9/2003 | Levin |
| 6,656,227 B2 | 12/2003 | Levin |
| 6,689,085 B1 | 2/2004 | Rubenstein et al. |
| 6,814,547 B2 | 11/2004 | Childers et al. |
| 6,827,682 B2 | 12/2004 | Bugge et al. |
| 6,845,267 B2 | 1/2005 | Harrison et al. |
| 6,846,168 B2 | 1/2005 | Davis et al. |
| 6,854,467 B2 | 2/2005 | Boekstegers |
| 6,875,192 B1 | 4/2005 | Saul et al. |
| 6,887,214 B1 | 5/2005 | Levin et al. |
| 6,894,456 B2 | 5/2005 | Tsukamoto et al. |
| 6,905,474 B2 | 6/2005 | Borgesen |
| 6,911,014 B2 | 6/2005 | Wentling et al. |
| 6,921,378 B2 | 7/2005 | O'Keefe et al. |
| 6,926,691 B2 | 8/2005 | Miethke |
| 6,939,111 B2 | 9/2005 | Huitt et al. |
| 6,945,949 B2 | 9/2005 | Wilk |
| 6,949,080 B2 | 9/2005 | Wolf et al. |
| 6,953,481 B2 | 10/2005 | Phelps et al. |
| 6,955,655 B2 | 10/2005 | Burbank et al. |
| 6,960,179 B2 | 11/2005 | Gura |
| 6,964,652 B2 | 11/2005 | Guiles et al. |
| 6,974,445 B2 | 12/2005 | Stergiopulos |
| 6,976,973 B1 | 12/2005 | Ruddell et al. |
| 6,979,351 B2 | 12/2005 | Forsell et al. |
| 6,981,964 B2 | 1/2006 | Rioux et al. |
| 6,994,700 B2 | 2/2006 | Elkins et al. |
| 7,011,095 B2 | 3/2006 | Wolf et al. |
| 7,017,340 B2 | 3/2006 | Chicky |
| 7,025,739 B2 | 4/2006 | Saul |
| 7,025,742 B2 | 4/2006 | Rubenstein et al. |
| 7,063,679 B2 | 6/2006 | Maguire et al. |
| 7,169,303 B2 | 1/2007 | Sullivan et al. |
| 7,195,608 B2 | 3/2007 | Burnett |
| 7,311,690 B2 | 12/2007 | Burnett |
| 7,335,179 B2 | 2/2008 | Burnett |
| 7,621,886 B2 | 11/2009 | Burnett |
| 7,670,332 B2 | 3/2010 | O'Keefe et al. |
| 7,909,790 B2 | 3/2011 | Burnett |
| 8,012,118 B2 | 9/2011 | Curtin et al. |
| 8,202,248 B2 | 6/2012 | Burnett et al. |
| 8,241,239 B2 | 8/2012 | Solomon et al. |
| 8,394,048 B2 | 3/2013 | Burnett |
| 8,398,577 B2 | 3/2013 | Burnett |
| 8,517,973 B2 | 8/2013 | Burnett |
| 8,585,635 B2 | 11/2013 | Degen et al. |
| 8,600,517 B2 | 12/2013 | Forsell |
| 8,612,013 B2 | 12/2013 | Forsell |
| 8,641,659 B2 | 2/2014 | Soykan et al. |
| 8,771,221 B2 | 7/2014 | Burnett |
| 8,882,699 B2 | 11/2014 | Burnett |
| 8,961,448 B2 | 2/2015 | Forsell |
| 8,965,523 B2 | 2/2015 | Forsell |
| 8,992,456 B1 | 3/2015 | Powell |
| 9,039,652 B2 | 5/2015 | Degen et al. |
| 9,138,521 B2 | 9/2015 | Solomon et al. |
| 9,138,523 B2 | 9/2015 | Burnett et al. |
| 9,144,660 B2 | 9/2015 | Degen |
| 9,149,613 B2 | 10/2015 | Degen et al. |
| D743,542 S | 11/2015 | Degen |
| D743,543 S | 11/2015 | Degen |
| 9,339,636 B1 | 5/2016 | Khan et al. |
| 9,421,347 B2 | 8/2016 | Burnett |
| 9,577,459 B2 | 2/2017 | Degen et al. |
| 9,675,327 B2 | 6/2017 | Johnson et al. |
| 9,694,165 B2 | 7/2017 | Forsell |
| 9,808,634 B2 | 11/2017 | Forsell |
| 9,913,968 B2 | 3/2018 | Burnett |
| 9,956,336 B2 | 5/2018 | Degen et al. |
| 10,252,037 B2 | 4/2019 | Degen et al. |
| 2002/0013545 A1 | 1/2002 | Soltanpour et al. |
| 2002/0022793 A1 | 2/2002 | Bertrand et al. |
| 2002/0123715 A1 | 9/2002 | Sorenson et al. |
| 2003/0114787 A1 | 6/2003 | Gura |
| 2003/0163079 A1 | 8/2003 | Burnett |
| 2003/0171710 A1 | 9/2003 | Bassuk et al. |
| 2003/0217962 A1 | 11/2003 | Childers et al. |
| 2003/0220606 A1 | 11/2003 | Busby et al. |
| 2004/0018228 A1 | 1/2004 | Fischell et al. |
| 2004/0049288 A1 | 3/2004 | Levin |
| 2004/0098113 A1 | 5/2004 | Forsell et al. |
| 2004/0126775 A1 | 7/2004 | Altieri et al. |
| 2004/0147871 A1 | 7/2004 | Burnett |
| 2005/0131340 A1 | 6/2005 | Sorenson et al. |
| 2005/0273034 A1 | 12/2005 | Burnett |
| 2006/0010014 A1 | 1/2006 | Brown |
| 2006/0024200 A1 | 2/2006 | Nishikiori et al. |

(56) References Cited

U.S. PATENT DOCUMENTS

| | | |
|---|---|---|
| 2006/0036208 A1 | 2/2006 | Burnett |
| 2006/0058731 A1 | 3/2006 | Burnett et al. |
| 2006/0094984 A1 | 5/2006 | Wood et al. |
| 2007/0055197 A1 | 3/2007 | Shakir |
| 2007/0106205 A1 | 5/2007 | Connell et al. |
| 2007/0228071 A1 | 10/2007 | Kamen et al. |
| 2007/0255345 A1 | 11/2007 | Krause |
| 2007/0299317 A1 | 12/2007 | Hoyme et al. |
| 2008/0108935 A1 | 5/2008 | Nyhart |
| 2008/0154173 A1 | 6/2008 | Burnett |
| 2008/0214983 A1 | 9/2008 | Mauge et al. |
| 2008/0230450 A1 | 9/2008 | Burbank et al. |
| 2009/0069642 A1 | 3/2009 | Gao et al. |
| 2009/0171241 A1 | 7/2009 | Garcia et al. |
| 2009/0198174 A1 | 8/2009 | Childers et al. |
| 2009/0275924 A1 | 11/2009 | Lattanzio et al. |
| 2009/0318844 A1 | 12/2009 | Burnett |
| 2010/0010832 A1 | 1/2010 | Boute et al. |
| 2010/0114012 A1 | 5/2010 | Sandford et al. |
| 2010/0215375 A1 | 8/2010 | Reams |
| 2010/0249692 A1 | 9/2010 | Dacey et al. |
| 2010/0312163 A1 | 12/2010 | Forsell |
| 2010/0312164 A1 | 12/2010 | Forsell |
| 2011/0025261 A1 | 2/2011 | Bersenev |
| 2011/0034986 A1 | 2/2011 | Chou et al. |
| 2011/0184339 A1 | 7/2011 | Tan |
| 2011/0184340 A1 | 7/2011 | Tan et al. |
| 2012/0209085 A1 | 8/2012 | Degen et al. |
| 2012/0209165 A1 | 8/2012 | Degen et al. |
| 2013/0199998 A1 | 8/2013 | Kelly et al. |
| 2013/0211322 A1 | 8/2013 | Degen et al. |
| 2013/0289334 A1 | 10/2013 | Badstibner et al. |
| 2014/0012180 A1 | 1/2014 | Levin et al. |
| 2014/0066841 A1 | 3/2014 | Degen et al. |
| 2015/0088090 A1 | 3/2015 | Macy, Jr. |
| 2016/0000984 A1 | 1/2016 | Burnett et al. |
| 2016/0022971 A1 | 1/2016 | Degen et al. |
| 2016/0331947 A1 | 11/2016 | Burnett |
| 2017/0128654 A1 | 5/2017 | Feld |
| 2017/0281848 A1 | 10/2017 | Axelsson et al. |
| 2017/0304597 A1 | 10/2017 | Forsell |
| 2018/0056050 A1 | 3/2018 | Degen et al. |
| 2018/0060520 A1 | 3/2018 | Degen et al. |
| 2018/0093081 A1 | 4/2018 | Forsell |

FOREIGN PATENT DOCUMENTS

| | | |
|---|---|---|
| EP | 0 366 389 A2 | 5/1990 |
| EP | 0 980 685 A2 | 2/2000 |
| EP | 1 362 605 A1 | 11/2003 |
| EP | 1 517 718 B1 | 3/2005 |
| EP | 1 539 294 B1 | 6/2005 |
| EP | 2 244 667 A1 | 11/2010 |
| EP | 2244662 A1 | 11/2010 |
| EP | 2244663 A1 | 11/2010 |
| EP | 2244758 A1 | 11/2010 |
| EP | 2244759 A1 | 11/2010 |
| EP | 2244760 A1 | 11/2010 |
| EP | 2 676 638 B1 | 12/2013 |
| EP | 2349473 B1 | 12/2016 |
| EP | 3275505 A1 | 1/2018 |
| EP | 2054105 B1 | 7/2018 |
| GB | 2 350 794 A | 12/2000 |
| JP | H04-327857 | 11/1992 |
| JP | 2004-513681 | 5/2004 |
| JP | A2005-171892 | 6/2005 |
| WO | WO-97/41799 A1 | 11/1997 |
| WO | WO-98/16171 A1 | 4/1998 |
| WO | WO-99/34116 A1 | 7/1999 |
| WO | WO-02/07596 A1 | 1/2002 |
| WO | WO-03/072166 A1 | 9/2003 |
| WO | WO-2004/012806 A1 | 2/2004 |
| WO | WO-2004/105730 A1 | 12/2004 |
| WO | WO-2005/018708 A1 | 3/2005 |
| WO | WO-2006/023589 A2 | 3/2006 |
| WO | WO-2008/055248 A1 | 5/2008 |
| WO | WO-2009/096854 A1 | 8/2009 |
| WO | WO-2010/077851 A2 | 7/2010 |
| WO | WO-2012/112664 A1 | 8/2012 |
| WO | WO-2013/122580 A1 | 8/2013 |
| WO | WO-2013/166038 A2 | 11/2013 |
| WO | WO-2014/140277 A1 | 9/2014 |
| WO | WO-2015/108782 A1 | 7/2015 |
| WO | WO-2018/037359 A1 | 3/2018 |

OTHER PUBLICATIONS

Int'l Search Report and Written Opinion dated Aug. 24, 2018 in Int'l PCT Patent Appl. Serial No. PCT/IB2018/053587.

Puttagunta, et al., Peritoneal Dialysis for Heart Failure, Peritoneal Dialysis International, 35(6):645-649 (2015).

Ruhi, et al., Use of Peritoneal Ultrafiltration in the Elderly Refractory Congestive Heart Failure Patients, Int. Urol. and Nephrol., 44(3):963-969 (2012).

U.S. Appl. No. 14/856,447, filed Sep. 16, 2015, Burnett et al.

U.S. Appl. No. 14/874,187, filed Oct. 2, 2015, Degen et al.

U.S. Appl. No. 15/965,727, filed Apr. 27, 2018, Degen et al.

U.S. Appl. No. 15/985,598, filed May 21, 2018, Inhaber et al.

Bellot, Pablo, et al., Automated low flow pump system for the treatment of refractory ascites: A multi-center safety and efficacy study, Journal of Hepatology, 58(5):922-927 (2013).

Costanzo et al., "Early Ultrafiltration in Patients with Decompensated Heart Failure and Diuretic Resistance," J. Am. Coll. Cardiol., (2005), vol. 46(11):2047-2051.

Fukuda, et al., Survivin, a cancer target with an emerging role in normal adult tissues, Mol. Cancer Ther., 5(5):1087-1098 (2006).

Hecking, et al., Sodium Setpoint and Sodium Gradient: Influence on Plasma Sodium Change and Weight Gain, Am J. Nephrol, 33(1):39-48 (2011).

Houlberg et al., "Terminal Right Heart Failure Due to Complex Congenital Cardiac Disease Successfully Managed by Home Peritoneal Drainage," Cardiol. Young, (2003), vol. 13(6):568-70.

International Search Report dated Sep. 16, 2008 in Int'l PCT Appl. Serial No. PCT/US2005/029305.

International Search Report & Written Opinion dated Mar. 18, 2013 in Int'l PCT Appl. Serial No. PCT/US2012/025188.

International Search Report & Written Opinion dated Jan. 4, 2018 in Int'l PCT Patent Appl. Serial No. PCT/IB2017/055092.

International Search Report & Written Opinion dated Apr. 16, 2015 in Int'l PCT Patent Appl. Serial No. PCT/US2015/010840.

Partial International Search dated Dec. 8, 2017 in Int'l PCT Patent Appl. No. PCT/IB17/55093.

Mc Causland, et al., Dialysate sodium, serum sodium and mortality in maintenance hemodialysis, Nephrol. Dial. Transplant, 27:1613-1618 (2012).

Medtronic Reveal LinqTM LNQ11, Insertable Cardiac Monitor, Clinician Manual, 98 pages (2015).

Munoz Mendoza, et al., Dialysate sodium and sodium gradient in maintenance hemodialysis: a neglected sodium restriction approach? Nephrol Dial Transplant, 26(4):1281-1287 (2011).

Nakayama, et al., Clinical Effect of Low Na Concentration Dialysate (120mEq/L) for CAPD Patients, Abstracts of the XIII Annual CAPD Conference, Peritoneal Dialysis International, vol. 13, Supplement 1, 1993.

Ortiz et al., "Long-Term Automated Peritoneal Dialysis in Patients with Refractory Congestive Heart Failure," Advances in Peritoneal Dialysis, (2003), vol. 19:77-80.

Rosenblit, et al., Peritoneal-Urinary Drainage for Treatment of Refractory Ascites: A Pilot Study, J. Vascular & Interv. Radiology, 9(6):998-1005 (1998).

Smyth, "Pump implant for cancer patients 'is a game-changer' for thousands", The Times, Health News, p. 11, Jan. 18, 2013.

www.medtronic.com/us-en/patients/treatments-therapies/fainting-heart-monitor/reveal-linq-icm.html (May 2017) (Accessed Nov. 27, 2017).

Zepeda-Orozco, et al., Dialysis Disequilibrium Syndrome, Pediatr. Nephrol, 27:2205-2211 (2012).

(56) References Cited

OTHER PUBLICATIONS

U.S. Appl. No. 10/369,550 / U.S. Pat. No. 7,335,179, filed Feb. 21, 2003 / Feb. 26, 2008.
U.S. Appl. No. 10/700,863 / U.S. Pat. No. 7,311,690, filed Nov. 3, 2003 / Dec. 26, 2007.
U.S. Appl. No. 10/826,237 / U.S. Pat. No. 7,909,790, filed Apr. 17, 2004 / Mar. 22, 2011.
U.S. Appl. No. 10/922,478 / U.S. Pat. No. 8,202,248, filed Aug. 18, 2004 / Jun. 19, 2012.
U.S. Appl. No. 11/181,539 / U.S. Pat. No. 7,621,886, filed Jul. 13, 2005 / Nov. 24, 2009.
U.S. Appl. No. 11/198,079 / U.S. Pat. No. 7,195,608, filed Aug. 4, 2005 / Mar. 27, 2007.
U.S. Appl. No. 11/933,214 / U.S. Pat. No. 8,398,577, filed Oct. 31, 2007 / Mar. 19, 2013.
U.S. Appl. No. 12/014,696 / U.S. Pat. No. 8,394,048, filed Jan. 15, 2008 / Mar. 12, 2013.
U.S. Appl. No. 13/029,069 / U.S. Pat. No. 8,517,973, filed Feb. 16, 2011 / Aug. 27, 2013.
U.S. Appl. No. 13/397,498 / U.S. Pat. No. 8,585,635, filed Feb. 15, 2012 / Nov. 19, 2013.
U.S. Appl. No. 13/397,509 / U.S. Pat. No. 9,149,613, filed Feb. 15, 2012 / Oct. 6, 2015.
U.S. Appl. No. 13/397,523 / U.S. Pat. No. 9,039,652, filed Feb. 15, 2012 / May 26, 2015.
U.S. Appl. No. 13/473,516 / U.S. Pat. No. 9,138,523, filed May 16, 2012 / Sep. 22, 2015.
U.S. Appl. No. 13/665,543 / U.S. Pat. No. 9,144,660, filed Oct. 31, 2013 / Sep. 29, 2015.
U.S. Appl. No. 13/789,250 / U.S. Pat. No. 8,771,221, filed Mar. 7, 2013 / Jul. 8, 2014.
U.S. Appl. No. 13/831,642 / U.S. Pat. No. 9,577,459, filed Mar. 15, 2013 / Feb. 21, 2017.
U.S. Appl. No. 13/973,981 / U.S. Pat. No. 8,882,699, filed Aug. 22, 2013 / Nov. 11, 2014.
U.S. Appl. No. 13/973,984 / U.S. Pat. No. 9,421,347, filed Aug. 22, 2013 / Aug. 23, 2016.
U.S. Appl. No. 14/077,005 / U.S. Pat. No. 9,956,336, filed Nov. 11, 2013 / May 1, 2018.
U.S. Appl. No. 14/155,079 / U.S. Pat. No. 9,673,527, filed Jan. 14, 2014 / Jun. 13, 2017.
U.S. Appl. No. 14/856,447, filed Sep. 16, 2015.
U.S. Appl. No. 14/874,187, filed Oct. 2, 2015.
U.S. Appl. No. 15/220,812 / U.S. Pat. No. 9,913,968, filed Jul. 27, 2016 / Mar. 13, 2018.
U.S. Appl. No. 15/249,192, filed Aug. 26, 2016.
U.S. Appl. No. 15/684,479, filed Aug. 23, 2017.
U.S. Appl. No. 15/965,727, filed Apr. 27, 2018.
U.S. Appl. No. 15/985,598, filed May 21, 2018.
International Search Report and Written Opinion dated Feb. 2, 2018 in Int'l PCT Patent Appl. No. PCT/IB2017/055093.

DIRECT SODIUM REMOVAL METHOD, SOLUTION AND APPARATUS TO REDUCE FLUID OVERLOAD IN HEART FAILURE PATIENTS

CROSS-REFERENCE TO RELATED APPLICATIONS

This application claims the benefit of priority of U.S. Provisional Application Ser. No. 62/510,652, filed May 24, 2017, the entire contents of which are incorporated herein by reference.

FIELD OF THE INVENTION

The present invention relates generally to use of a no or low sodium infusate that is administered to a patient's peritoneal cavity to directly remove sodium, and thereby fluid from the body to alleviate fluid overload in heart failure patients with residual renal function, hereinafter, a DSR infusate. The methods, DSR infusate and apparatus work to remove excess fluid through the removal of sodium. Sodium is moved to the peritoneal cavity through one or both of: 1) ultrafiltration and/or 2) diffusion down a steep concentration gradient, from where it is subsequently eliminated. Fluid is eliminated from the body to maintain a relatively stable serum sodium concentration, by one or both of: 1) inducing osmotic ultrafiltration to move fluid from the patient's body into the peritoneal cavity, from where it is eliminated and/or 2) enhancing the excretion of excess fluid via the kidneys through urination.

BACKGROUND

Patients suffering from any of a number of forms of heart failure are prone to the accumulation of additional sodium in body tissues and resultingly, increased fluid in the body. For example, in congestive heart failure, due to dysfunction of the left side or right side of the heart, or both, the body is unable to pump blood with normal efficiency, leading to the reduction in systemic circulation that can result in retention of sodium and stasis or pooling of blood or fluid in the lungs or liver, edema and/or cardiac hypertrophy.

The Centers for Disease Control and Prevention (CDC) estimates that about 5.7 million people in the United States suffer from some form of heart failure. Heart failure is generally categorized into four different stages with the most severe being end stage heart failure. End stage heart failure may be diagnosed where a patient has heart failure symptoms at rest in spite of medical treatment. Patients may have systolic heart failure, characterized by decreased ejection fraction. In patients with systolic heart failure, the walls of the ventricle are weak and do not squeeze as forcefully as in a healthy patient. Consequently, during systole a reduced volume of oxygenated blood is ejected into circulation, a situation that continues in a downward spiral until death. Patients alternatively may have diastolic heart failure, in which stiffened or thickened myocardium makes it difficult for the affected heart chamber to fill with blood. A patient diagnosed with end stage heart failure has a one-year mortality rate of approximately 50%.

Renal failure, also referred to as chronic kidney disease ("CKD"), is diagnosed by blood tests that measure blood urea nitrogen ("BUN") and creatinine, enabling estimation of glomerular filtration rate ("GFR"). GFR is an overall index of kidney function that is calculated by any of a number of well-known formulae, such as CKD-EPI creatinine equation (2009) or CKD-EPI creatinine-cystatin equation (2012) and takes into account a patient's serum creatinine, age, gender and race. For example, the GFR may be computed using the CKD-EPI creatinine equation (2009) as follows:

$$eGFR = 141 \times \min(S_{Cr}/\kappa, 1)^{\alpha} \times \max(S_{Cr}/\kappa, 1)^{-1.209} \times 0.993^{Age} \times 1.018 \text{ [if female]} \times 1.159 \text{ [if Black]}$$

wherein:
eGFR (estimated glomerular filtration rate)=mL/min/1.73 m$^2$
$S_{Cr}$ (standardized serum creatinine)=mg/dL
$\kappa$=0.7 (females) or 0.9 (males)
$\alpha$=−0.329 (females) or −0.411 (males)
min=indicates the minimum of $S_{Cr}/\kappa$ or 1
max=indicates the maximum of $S_{Cr}/\kappa$ or 1
age=years The foregoing equation is available on the National Kidney Foundation website at https://www.kidney.org/content/ckd-epi-creatinine-equation-2009.

Generally, assessment of the severity of CKD is based on the computed GFR value in conjunction with the following table:

| Stage | Description | GFR (mL/min/1.73 m$^2$) |
|---|---|---|
| At increased risk | Risk factors for kidney disease (e.g., diabetes, high blood pressure, family history, older age, ethnic group) | >90 |
| 1 | Kidney damage with normal kidney function | ≥90 |
| 2 | Kidney damage with mild loss of kidney function | 89 to 60 |
| 3a | Mild to moderate loss of kidney function | 59 to 44 |
| 3b | Moderate to severe loss of kidney function | 44 to 30 |
| 4 | Severe loss of kidney function | 29 to 15 |
| 5 | Kidney failure | <15 |

Typically, a patient with severely reduced kidney function, generally stage 5, will receive dialysis to remove metabolic waste from the blood when the kidneys can no longer do so adequately. Dialysis may be accomplished using either an extracorporeal machine or peritoneal dialysis. In the first option, the patient is coupled to a hemodialyzer, in which case blood is routed from the body to an extracorporeal machine, cleansed, and then returned to the patient's body. In peritoneal dialysis, a cleansing fluid or dialysate is infused into the patient's abdomen, where it causes metabolic waste to pass from the abdominal arteries and veins into the dialysate for a specified period of time, e.g., 30-45 minutes, after which the dialysate is drained from the abdomen and discarded. Typically, the patient may repeat this process between three and five times each 24-hour period.

Low sodium dialysates are known for use in patients with end-stage renal disease requiring dialysis to treat CKD. For example, U.S. Pat. No. 5,589,197 to Shockley et al. describes a dialysate for use in peritoneal dialysis wherein the sodium concentration is between about 35 to 125 meq/L. As explained in that patent, the sodium concentration in the solution may be decreased to a level below the patient's plasma concentration of sodium, thus causing sodium to be transported from the circulation to the peritoneal cavity. Unfortunately, problems were encountered with such low sodium dialysates, including symptomatic drops in blood pressure, and in some cases dialysis disequilibrium syndrome, a potentially fatal complication resulting in cerebral edema, coma and death. See, e.g., Nakayma, *Clinical Effect of Low Na Concentration Dialysate* (120 *mEq/L) for CAPD Patients*, PD Conference, San See, e.g., Zepeda-Orozco D, Quigley R., *Dialysis disequilibrium syndrome*, Pediatric Nephrology (Berlin, Germany) 2012; 27(12):2205-2211.

In view of the past experience with low sodium dialysates, people with end-stage kidney disease who receive dialysis on a regular basis rely on therapy to optimize salt and water levels. The reported current average concentration of sodium in dialysate is generally about 132 mMol/L. See, e.g., Hecking M, Kainz A, Horl W H, Herkner H, Sunder-Plassmann G., *Sodium setpoint and sodium gradient: influence on plasma sodium change and weight gain*. American Journal of Nephrology 2011; 33(1):39-48; Mc Causland F R, Brunelli S M, Waikar S S., *Dialysate sodium, serum sodium and mortality in maintenance hemodialysis*. Nephrology Dialysis Transplantation 2012; 27(4):1613-8.

Decades of experience with dialysate sodium concentrations that are higher than patients' blood sodium levels show that such dialysates facilitate fluid removal without removal of sodium during dialysis and improve the likelihood of maintaining normal BP and heart function during dialysis. However, higher sodium levels also result in people on hemodialysis often dialyzing with a positive sodium gradient between their blood and the dialysate. See, e.g., Munoz Mendoza J, Sun S, Chertow G, Moran J, Doss S, Schiller B., *Dialysate sodium and sodium gradient in maintenance hemodialysis: a neglected sodium restriction approach?*, Nephrology Dialysis Transplantation 2011; 26(4):1281-7. Accordingly, patients often gain sodium by the end of a dialysis session, resulting in increased thirst, fluid consumption and hypertension. As such, the net result for patients having multiple weekly hemodialysis sessions is chronic sodium and water overload.

Applicants have observed that eliminating fluid overload is a key clinical objective in heart failure, and that fluid overload can lead to serious clinical complications including dyspnea. Achieving effective reduction of fluid requires the elimination of sodium from the body, as the body will act to maintain a constant serum osmolality and to maintain its sodium levels, as described for example, in Guyton & Hall, Textbook of Medical Physiology. Accordingly, it would be desirable to develop a method for using no or low sodium infusates to remove sodium and thereby fluid from the patient to treat fluid overload in heart failure patients.

SUMMARY OF THE INVENTION

The present invention is directed to methods of treating fluid overload in heart failure patients with residual renal function using a no or low sodium DSR infusate administered to the peritoneal cavity to remove sodium and thereby fluid from the patients' body to alleviate fluid overload. Sodium is moved to the peritoneal cavity through one or both of: 1) ultrafiltration and/or 2) diffusion down a steep concentration gradient, from where it is subsequently eliminated. Fluid is eliminated from the body to maintain a relatively stable serum sodium concentration, by one or both of: 1) inducing osmotic ultrafiltration to move fluid (osmotic ulfiltrate) from the patient's body into the peritoneal cavity, from where it is eliminated and/or 2) enhancing the excretion of excess fluid via the kidneys through urination. As such, the present invention eliminates sodium from the body and thereby fluid to maintain relatively stable serum sodium concentrations, reducing fluid overload and edema, while preventing hyponatremia.

In accordance with the principles of the present invention, a patient suffering from heart failure is treated (either intermittently or continuously) with a low sodium or no sodium DSR infusate administered to the peritoneal cavity. The DSR infusate, which in an exemplary form may comprise a D-10 dextrose solution, i.e., 10 grams dextrose per 100 ml of aqueous solution, is allowed to remain in the peritoneal cavity for a predetermined period before it is removed, and then is extracted together with sodium that moves from the patient's body into the peritoneal cavity and the osmotic ultrafiltrate. The proposed direct sodium removal ("DSR") method constitutes a radical departure from conventional peritoneal dialysis, in that it is designed specifically to treat fluid overload in heart failure patients, rather than attempting to remove toxins and accumulated metabolic byproducts by cleansing the tissues with a dialysate, as in conventional peritoneal dialysis.

In accordance with one aspect of the invention, the inventive DSR method, infusates and apparatus are expected to be suitable for use in heart failure patients suffering from fluid overload who generally demonstrate a GFR value greater than 15 mL/min/1.73 m$^2$ and should exhibit kidney function from normal to CKD Stage 4. In patients with CKD of Stage 5 or GFR<15 ml/min/1.73 m$^2$, use of a no or low sodium DSR infusate with volumes adequate for dialysis would result in dangerous or terminal hyponatremia and reduction in plasma volume leading to hemodynamic collapse. Conversely, use of small volumes of a no or low sodium DSR infusate to avoid hyponatremia in these patients who needed dialysis would not provide sufficient removal of waste products, and may result in uremia. In other words, patients suitable for direct sodium removal using the method of the present invention would be patients not normally eligible for dialysis for the purpose of CKD treatment.

In particular, due to concern regarding symptomatic blood pressure drop, as well as hyponatremia and related effects, patients normally eligible for dialysis with end-stage kidney insufficiency, exhibiting CKD of Stage 5 or GFR less than or equal to 15 mL/min/1.73 m$^2$ specifically should be excluded from the pool of patients eligible for use with the DSR methods of the present invention.

The proposed methods of using a no or low sodium DSR infusate in accordance with the principles of the present invention may be accomplished with the implantable pump system described in commonly-assigned U.S. Patent Application Publication No. US2014/0066841, the contents of which are incorporated herein by reference. That published application describes a system for ambulatory peritoneal dialysis in which a patient infuses a dialysate into the abdomen, and after a predetermined time and at predetermined intervals, an implantable pump transfers volumes of dialysate to the patient's bladder, where it may be excreted through urination. In accordance with the principles of the present invention, the process is performed not to address or even principally address CKD. Instead, the process is performed with a no or low sodium DSR infusate to remove sodium in heart failure patients suffering from fluid overload who retain residual renal function. As a result, fluid is removed from the body through i) urination (as a result of the remaining kidney function) and ii) direct removal of the osmotic ultrafiltrate, to restore serum sodium concentrations and reduce fluid overload and edema, while preventing hyponatremia.

BRIEF DESCRIPTION OF THE DRAWINGS

FIGS. 6A, 6B, 6C and 6D are, respectively, an exploded perspective view of the drive assembly of the implantable device; front and plan views of the upper housing; and a perspective view of the manifold of an exemplary embodiment of the implantable device.

DETAILED DESCRIPTION OF THE INVENTION

Figure 1A:
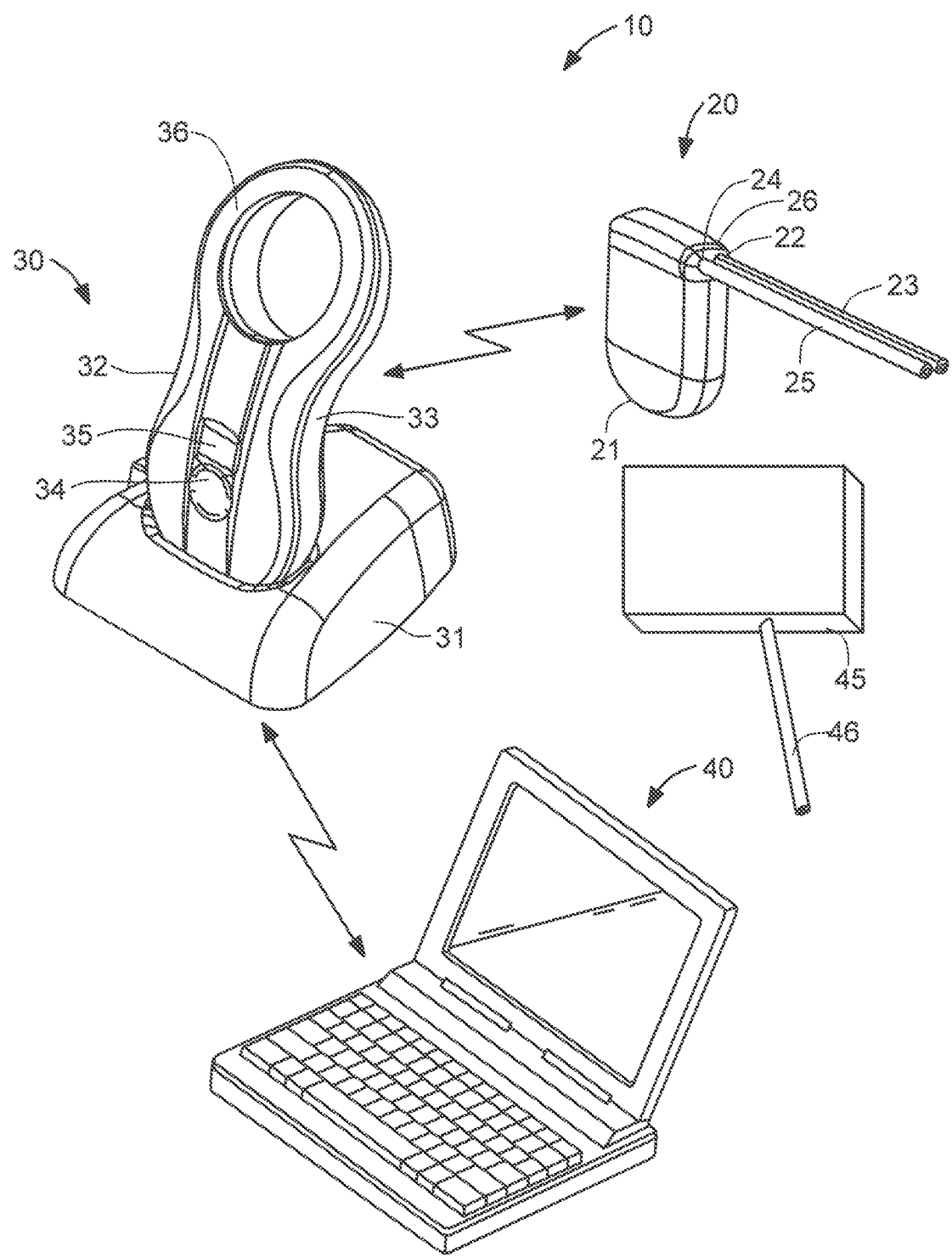
FIG. 1A is a perspective view of an exemplary system for implementing the methods of the present invention in a heart failure patient with residual renal function suffering from fluid overload.

The present invention is directed to methods of treating fluid overload in various forms of heart failure, such as left heart or right heart dysfunction. In accordance with the principles of the present invention, a heart failure patient with residual renal function suffering from fluid overload is treated with a no or low sodium DSR infusate administered to the peritoneal cavity. The low sodium concentration in the DSR infusate causes sodium and fluid (osmotic ultrafiltrate) to pass from the patient's body into the peritoneal cavity. The DSR infusate is allowed to remain, or dwell, in the peritoneal cavity for a pre-determined period before it is removed, together with the extracted sodium and the osmotic ultrafiltrate. Removal of the sodium-laden DSR infusate and osmotic ultrafiltrate from the peritoneal cavity may be performed using an implantable system, such as the Alfapump commercialized by Sequana Medical AG, Zurich, Switzerland.

As used in this disclosure, a no or low sodium DSR infusate has a sodium content of less than 120 meq/L, more preferably, less than 35 meq/L, and includes infusates having virtually zero concentration of sodium. Accordingly, the fluid overload treatment methods of the present invention specifically contemplate use of the inventive methods in heart failure patients having residual kidney function, and thus not in kidney failure. As used in this specification, residual kidney function corresponds to patients having a GFR value greater than 15 ml/min/1.73 m$^2$ or kidney function from normal to CKD of Stage 4.

Exemplary DSR infusate formulations in accordance with the principles of the present invention include D-0.5 to D-50 solutions, i.e., from 0.5 to 50 grams of dextrose per 100 ml of aqueous solution; Icodextrin solutions having from 0.5 to 50 grams of icodextrin per 100 ml of aqueous solution; high molecular weight glucose polymer solutions (weight average molecular weight Da>10,000) having from 0.5 to 50 grams of high molecular weight glucose polymer per 100 ml of aqueous solution, and combinations thereof. The aqueous solution includes at least purified water, and may in addition include electrolytes such as low amounts of magnesium or calcium salts, preservatives, ingredients having antimicrobial or antifungal properties, or buffering materials to control pH of the infusate. It is expected that Icodextrin, a high molecular weight glucose polymer, or other high molecular weight glucose polymer (weight average molecular weight, Da>10,000) may be preferable to dextrose because it has been observed to experience a lower rate of uptake when employed in a peritoneal dialysis setting, and thus may provide reduced serum glucose concentrations compared to a dextrose-based DSR solutions.

It is expected that the no or low sodium DSR infusate described herein should not be used on all heart failure patients with fluid overload, particularly those with little residual renal function, as the result could be fatal. For example, it is expected that use of the methods and DSR infusate of the present invention on heart failure patients having a GFR value lower than 15 or CKD of Stage 5, may result in severe hyponatremia and hypotension. Accordingly, for safety reasons, patients suffering from heart failure but also in kidney failure, or with a GFR less than or equal to 15 ml/min/1.73 m² or CKD of Stage 5 are contraindicated for use with the methods of treatment described herein.

Although it is contemplated that the inventive methods and DSR infusate may be used to treat fluid overload in heart failure with conventional peritoneal infusion and drainage techniques, it is expected that practice of the present invention may be particularly advantageously implemented using the implantable pump system offered by the assignee of the present application. Specifically, the Alfapump system, offered by Sequana Medical AG, Zurich, Switzerland, is well suited for treating heart failure using a peritoneal infusion mode of operation. In accordance with one aspect of the present invention, the no or low sodium DSR infusate is introduced into the peritoneal cavity, where the zero or low sodium concentration causes sodium and osmotic ultrafiltrate to pass from the patient's body into the peritoneal cavity. At predetermined times after infusion of the DSR infusate, and for predetermined intervals, the implantable pump may be activated, in accordance with a clinician's programmed instructions, to pump the sodium-laden DSR infusate and osmotic ultrafiltrate to the patient's bladder at a predetermined flow rate. Removal of sodium from the body leads to the removal of fluid by i) the functioning kidneys through urination and ii) accumulation of osmotic ultrafiltrate directly into the peritoneal cavity, which is then removed to the bladder via the implantable pump. In this manner, sodium and fluid is removed, while maintaining appropriate and stable serum sodium concentrations. Further, it is expected that after a DSR session, fluid will continue to accumulate in the peritoneal cavity as a result of the fluid overload, and the implantable pump may be programmed to pump such fluid to the bladder on a regular basis. The fluid accumulating in the peritoneal cavity is expected to contain sodium so the removal of such fluid to the bladder will lead to a further reduction of fluid overload in these patients.

The methods of the present invention therefore provide a method of controlling fluid overload and edema in heart failure patients while permitting such patients to experience a more normal lifestyle, untethered from frequent visits to a hospital or other medical facility. Advantageously, because the methods of the present invention lead to a reduction in fluid volume, the patient not only may experience improved comfort and lifestyle, but also forestalled co-morbidities, such as advancing chronic kidney disease and progressive heart failure.

An exemplary implantable system for practicing the method of the present invention is described in greater detail below as including an implantable pump that is specially configured to move fluid out of the peritoneal cavity and into the bladder, and that includes a plurality of sensors for monitoring and recording operating parameters relevant to the health of the patient. An externally held charging and communication system periodically charges and communicates with the implantable device, and downloads from the device the recorded operating parameters. Monitoring and control software on the treating physician's computer receives the recorded operating parameters from the charging and communication system, and allows the physician to modify the operation of the implantable device based on the physician's perception of the patient's health as reflected in the recorded operating parameters. Optionally, the monitoring and control software may be configured to alert the physician as to a prediction or detection of infection, heart failure decompensation or other clinical events based on the recorded operating parameters. The implantable device optionally may also include one or more ultraviolet (UV) sources configured to inhibit infection.

Overview of an Exemplary System for Implementing the Inventive Method

Referring to FIG. 1A, an overview of selected components of exemplary system 10 for use in practicing the methods of the present invention is provided. In FIG. 1A, components of the system are not depicted to scale on either a relative or absolute basis. System 10 comprises implantable device 20, external charging and communication system 30, software-based monitoring and control system 40, and optionally, DSR infusate reservoir 45. In the illustrated embodiment, monitoring and control system 40 is installed and run on a conventional laptop computer, tablet or smartphone, as may be used by the patient's physician. During patient visits, charging and communication system 30 may be coupled, either wirelessly or using a cable, to monitoring and control system 40 to download for review data stored on implantable device 20, or to adjust the operational parameters of the implantable device. Monitoring and control system 40 also may be configured to upload and store date retrieved from charging and communication system 30 to a remote server for later access by the physician or charging and communications system 30.

Implantable device 20 comprises an electromechanical pump having housing 21 configured for subcutaneous implantation. As described in further detail below with reference to FIG. 1C, implantable device 20 may include an electrically-driven mechanical gear pump as well as second pump connector 22 and first pump connector 24 configured to reduce the risk of improper installation and inadvertent disconnection, and may additionally include distinct cross-sections that further reduce the risk of improper installation. Catheter 46 and bladder catheter 25 are coupled to pump housing 21 and in some embodiments may be coupled to pump housing 21 using first pump connector 24. Peritoneal catheter 23 is coupled to pump housing 21 and may be coupled to pump housing 21 using second pump connector 22. DSR infusate is provided to the patient's peritoneal cavity from reservoir 45. Peritoneal catheter 23 comprises a tube having a first (proximal) end configured to be coupled to pump housing 21 and a second (distal) end configured to be positioned in the peritoneal cavity. Bladder catheter 25 comprises a tube having a first (proximal) end configured to be coupled to pump housing 21 and a second (distal) end configured to be inserted through the wall of, and fixed within, a patient's bladder. In a preferred embodiment, both catheters are made of medical-grade silicone and include polyester cuffs at their distal ends (not shown) to maintain the catheters in position.

Optional reservoir 45 is configured to deliver the no or low sodium DSR infusate to the patient's peritoneal cavity via catheter 46, which may have similar construction to the peritoneal catheter described further below with respect to FIGS. 2A-2B. In embodiments described further below with reference to FIG. 1B, the proximal end of catheter 46 may be configured to be removably coupled to external reservoir 45 via an appropriate coupling allowing the patient to easily exchange a depleted reservoir for a fresh one, and the distal end of catheter 46 may be configured for implantation in the patient's peritoneal cavity, with a tissue cuff (not shown) to promote tissue ingrowth at the point at which catheter 46 crosses the wall of the patient's skin and/or peritoneum. The distal end of catheter 46 may have a plurality of holes or apertures defined therein, like those discussed below with reference to FIG. 2B. Reservoir 45 may deliver the DSR infusate to the peritoneal cavity by any suitable mechanism, such as gravity or by operation of an extracorporeal pump (not shown). For example, an external pump may be used to facilitate DSR infusate flow from the reservoir 45 to the peritoneal cavity, or the reservoir may be physically raised above the level of the peritoneal cavity such that gravity draws the DSR infusate into the peritoneal cavity via catheter 46.

Figure 1B:
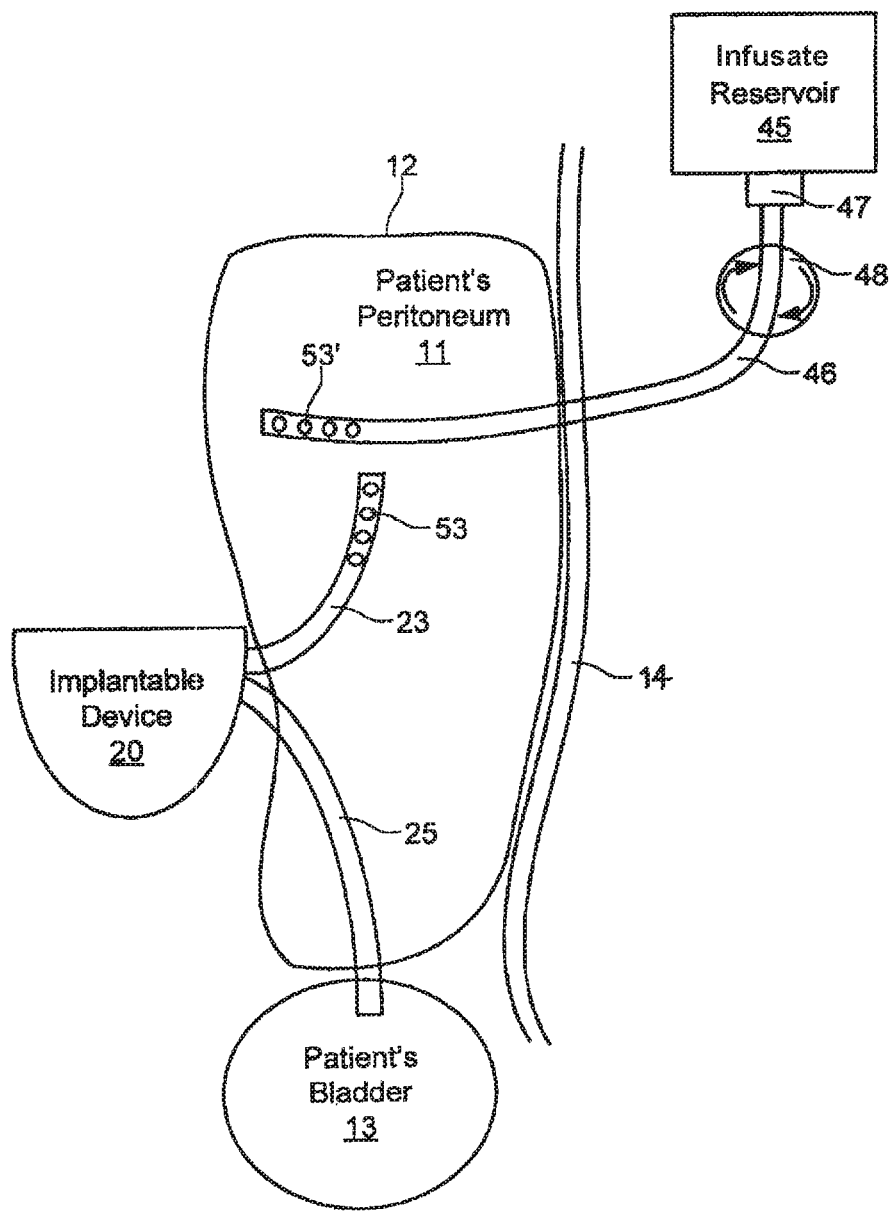
FIG. 1B is a plan view of selected components of the system of FIG. 1A as implanted in a patient.
Figure 1C:
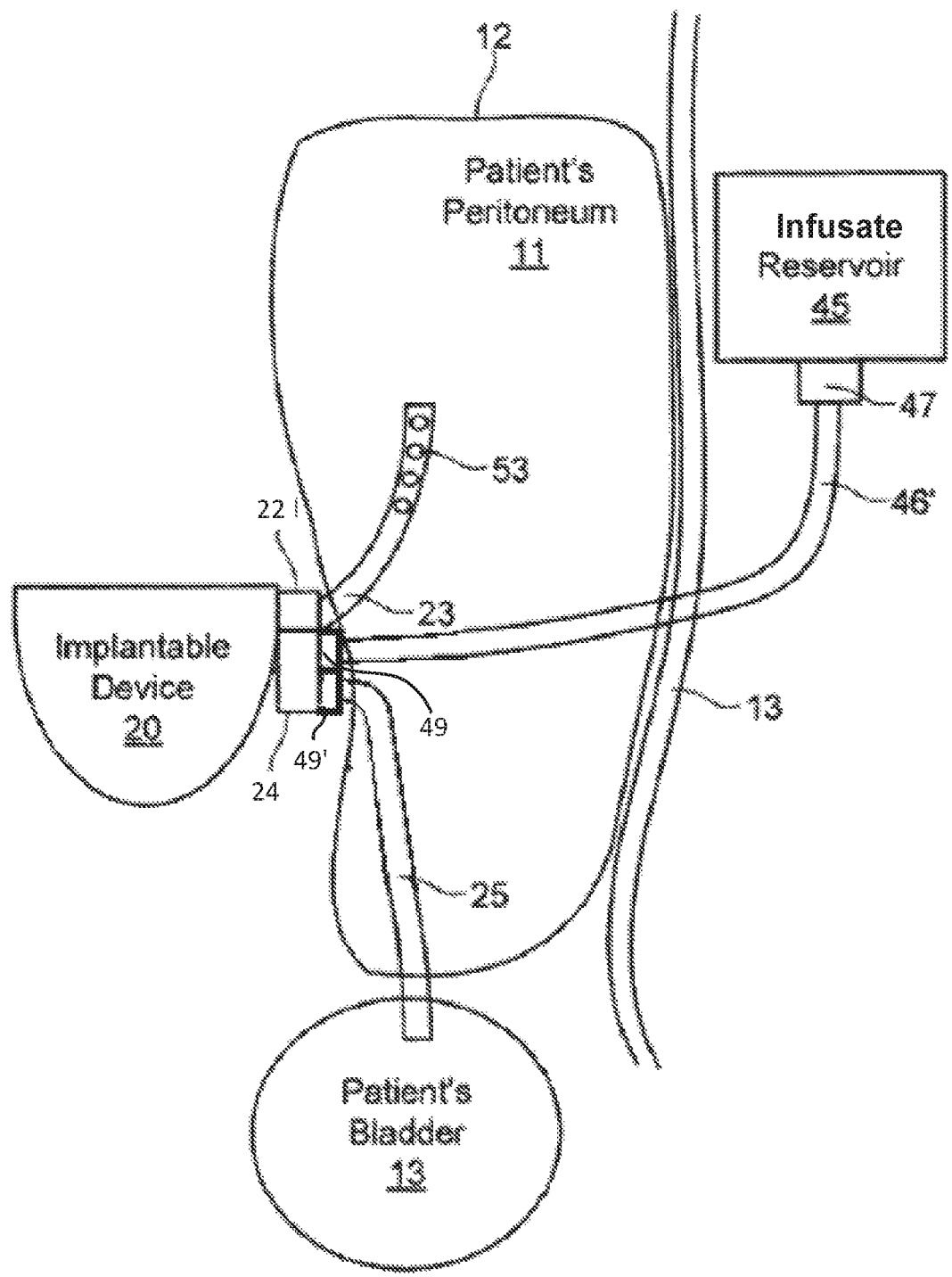
FIG. 1C is a plan view of selected components of an alternative embodiment of an exemplary system for practicing the methods of the present invention.

In the embodiment of FIG. 1C, the distal end of reservoir catheter 46' instead may be attached to first pump connector 24 of implantable device 20, and implantable device 20 may be configured to pump the DSR infusate from reservoir 45 into the peritoneal cavity via reservoir catheter 46' and peritoneal catheter 23. In such embodiments, reservoir 45 may be external or implantable, and implantable device 20 further may include one or more passive or active valves to prevent fluid from leaking from the reservoir into the bladder and from being pumped out of the bladder and into the peritoneal cavity at the same time that fluid is pumped from the reservoir and into the peritoneal cavity. The passive or active valves may also prevent sodium-laden DSR infusate and osmotic filtrate from being pumped out of the peritoneal cavity into the reservoir at the same time that such fluid is pumped from the peritoneal cavity into the bladder. Alternatively, the one or more passive or active valves may be positioned within reservoir catheter 46', peritoneal catheter 23 and/or bladder catheter 25.

Preferably, implantable device 20 is configured to move the sodium-laden DSR infusate and osmotic ultrafiltrate from the peritoneal cavity to the bladder in quantities, intervals and flow rates selected to provide sufficient time for the targeted amount of sodium to accumulate in the DSR infusate resulting in a reduction of sodium in the body leading to the removal of fluid by i) the functioning kidneys (through urination) and ii) direct removal to the bladder of the osmotic ultrafiltrate from the peritoneal cavity thereby reducing fluid overload and edema resulting from heart failure. Treatment algorithms may be developed with different formulations and volumes of no or low sodium DSR infusates, different lengths of dwell period and different rates of removal to the bladder. In general, pumping for short but frequent intervals is expected to inhibit the accumulation of material on the interior lumens of catheters 23 and 25, and reduce the risk of tissue ingrowth. The fluid circuit of implantable device 20 may be configured to provide an average flow rate of about 1-2.5 liters/hour, although much higher and lower flow rates are possible if needed. As described in detail below, the pumping time, flow rate and volume, including the time the DSR infusate is allowed to remain in the peritoneal cavity, may be programmed by the physician using monitoring and control system 40 as required for a specific patient.

Implantable device 20 may include pressure sensors that monitor pressure in one or both of the peritoneal cavity and the bladder, such that fluid is pumped from the peritoneal cavity to the bladder if the intra-abdominal pressure exceeds a limit determined by the physician. Alternatively or in addition, the output of the pressure sensors may cause pumping of fluid into the bladder to be disabled until the bladder is determined to have sufficient space to accommodate additional fluid. For patient comfort, implantable device 10 optionally may be programmed not to pump at night or when an accelerometer included in the implantable device indicates that the patient is asleep (and thus unlikely to be able to void the bladder). Implantable device 20 preferably includes multiple separate fail-safe mechanisms, to ensure that urine cannot pass from the bladder to the peritoneal cavity through the pump, thereby reducing the risk of transmitting infection.

Still referring to FIG. 1A, the external charging and communication system 30 of the exemplary system, in a preferred form, includes base 31 and handpiece 32. In this embodiment, handpiece 32 contains a controller, a radio transceiver, an inductive charging circuit, a battery, a quality-of-charging indicator and a display, and is removably coupled to base 31 to recharge its battery. Base 31 may contain a transformer and circuitry for converting conventional 120V or 220-240V service to a suitable DC current to charge handpiece 32 when coupled to base 31. In alternative embodiments, handpiece 32 may include such circuitry and a detachable power cord, thereby permitting the handpiece to be directly plugged into a wall socket to charge the battery. In a preferred embodiment, each of implantable device 20 and handpiece 32 includes a device identifier stored in memory, such that handpiece 32 provided to the patient is coded to operate only with that patient's specific implantable device 20.

Handpiece 32 preferably includes housing 33 having multi-function button 34, display 35, a plurality of light emitting diodes (LEDs, not shown) and inductive coil portion 36. Multi-function button 34 provides the patient the ability to issue a limited number of commands to implantable device 20, while display 35 provides visible confirmation that a desired command has been input; it also displays battery status. Inductive coil portion 36 houses an inductive coil that is used transfer energy from handpiece 32 to recharge the battery of implantable device 20. The LEDs, which are visible through the material of housing 33 when lit, may be arranged in three rows of two LEDs each, and are coupled to the control circuitry and inductive charging circuit contained within handpiece 32. The LEDs may be arranged to light up to reflect the degree of inductive coupling achieved between handpiece 32 and implantable device 20 during recharging of the latter. Alternatively, the LEDs may be omitted and an analog display provided on display 35 indicating the quality of inductive coupling.

Control circuitry contained within handpiece 32 is coupled to the inductive charging circuit, battery, LEDs and radio transceiver, and includes memory for storing information from implantable device 20. Handpiece 32 also preferably includes a data port, such as a USB port, that permits the handpiece to be coupled to monitoring and control system 40 during visits by the patient to the physician's office. Alternatively, handpiece 32 may include a wireless chip, e.g., conforming to the Bluetooth or IEEE 802.11 wireless standards, thereby enabling the handpiece to communicate wirelessly with monitoring and control system 40, either directly or via the Internet.

Monitoring and control system 40 is intended primarily for use by the physician and comprises software configured to run on a conventional computer, e.g., a laptop as illustrated in FIG. 1A or tablet or smartphone. The software enables the physician to configure, monitor and control operation of charging and communication system 30 and implantable device 20. The software may include routines for configuring and controlling pump operation, such as a target amount of fluid to move daily or per motor actuation, intervals between pump actuation, and limits on peritoneal cavity pressure, bladder pressure, pump pressure, and battery temperature. System 40 also may provide instructions to implantable device 20 via charging and control system 30 to control operation of implantable device 20 so as not to move fluid during specific periods (e.g., at night) or to defer pump actuation if the patient is asleep. System 40 further may be configured, for example, to send immediate commands to the implantable device to start or stop the pump, or to operate the pump in reverse or at high power to unblock the pump or associated catheters. The software of system 40 also may be configured to download real-time data relating to pump operation, as well as event logs stored during operation of implantable device 20. Based on the downloaded data, e.g., based on measurements made of the patient's intra-abdominal pressure, respiratory rate, and/or fluid accumulation, the software of system 40 optionally may be configured to alert the physician to a prediction or detection of heart failure decompensation and/or a change in the patient's health for which an adjustment to the flow rate, volume, time and/or frequency of pump operation may be required. Finally, system 40 optionally may be configured to remotely receive raw or filtered operational data from a patient's handpiece 32 over a secure Internet channel.

Figure 1D:
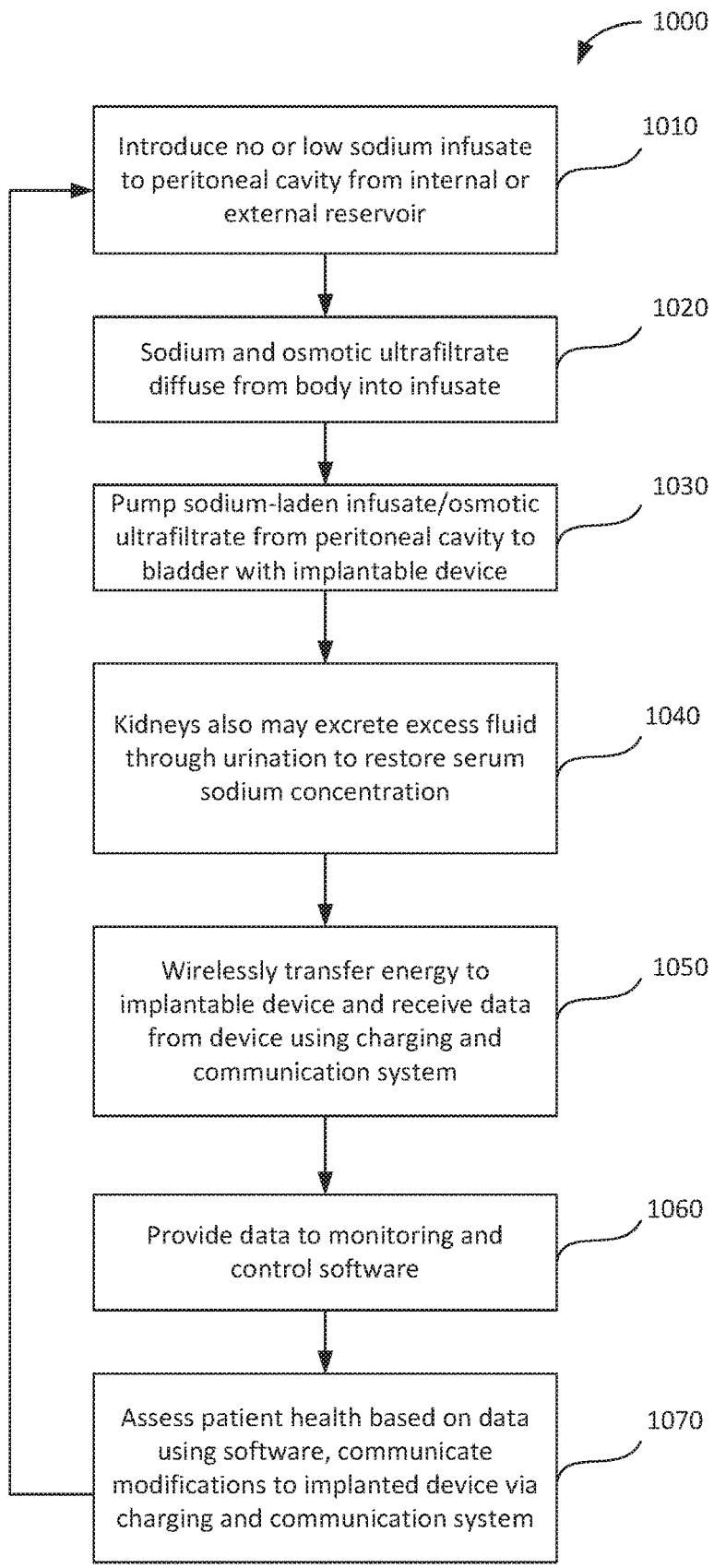
FIG. 1D illustrates steps of an exemplary method in accordance with the principles of the present invention using the system of FIGS. 1A-1C.

Turning now to FIGS. 1B-1D, various configurations of implantable device 20 and optional DSR infusate reservoir 45 are now described. Methods of using system 10 in accordance with the present invention to treat a heart failure patient suffering from fluid overload are provided with reference to FIG. 1D.

Referring now to FIG. 1B, an exemplary use of implantable device 20 for implementing the methods of the present invention is described. Device 20 is implanted subcutaneously, preferably outside of the patient's peritoneal cavity 11 as defined by peritoneal membrane 12, but beneath skin 13 so that the device may readily be charged by, and communicate with, charging and communication system 30 illustrated in FIG. 1A. Device 20 is coupled via appropriate connectors (not shown) to peritoneal catheter 23 and bladder catheter 25. Peritoneal catheter 23 is configured for implantation in the patient's peritoneal cavity 11 and preferably includes apertures 53 such as described in further detail below with reference to FIGS. 2A-2B. Bladder catheter 25 is configured for implantation in the patient's bladder 13 and preferably includes an anchor to secure the outlet end of the catheter within the bladder 13, such as described in further detail below with reference to FIGS. 3A-3B.

Optional DSR infusate reservoir 45 is positioned outside of the body, coupled to the peritoneal cavity via catheter 46. Catheter 46 is coupled to reservoir 45 via connector 47, which is configured so as to allow the patient to periodically replace reservoir 45 with ease. Catheter 46 preferably includes apertures 53', which may be similar in dimension and density to apertures 53, and which allow the DSR infusate to flow into the peritoneal cavity 11 in a relatively diffuse manner. Optional external pump 48 may be configured to cause the DSR infusate to flow from reservoir 45 into the peritoneal cavity 11 at a desired rate. For example, reservoir 45 may be positioned on a belt (not shown) that is worn around the patient's waist and includes pump 48. Pump 48 may be configured to communicate wirelessly with implantable device 20 so as to coordinate delivery of DSR infusate into the patient's peritoneal cavity.

In an alternative embodiment, DSR infusate reservoir 45 is positioned at a level above the peritoneal cavity 11 such that gravity causes the DSR infusate to flow from reservoir 45 into the peritoneum at a desired rate. In yet another embodiment, a pressurized container may be configured in combination with a controlled valve or a calibrated flow restriction device to deliver a predefined flow rate without the use of a pump. In this manner the delivery of the DSR infusate may be passive without the need for electronics or a pump. Delivery of a predefined amount of the DSR infusate may be recognized by the implantable device based on pressure increase within the peritoneal cavity, use of a flow meter, or other suitable measurement system.

In the embodiments discussed above, reservoir 45 preferably provides DSR infusate to peritoneal cavity 11 in a volume, at a rate, and with a frequency suitable to sufficiently fill the peritoneal cavity with the DSR infusate to treat or alleviate the fluid overload of the heart failure patient.

Alternatively, as illustrated in FIG. 1C, optional DSR infusate reservoir 45 may be positioned outside of the patient's body, e.g., using a belt or harness, and may be coupled to implantable device 20 via catheter 46' and connector 47. Implantable device 20 is configured to pump DSR infusate into peritoneal cavity 11 from reservoir 45 via catheters 46' and 23, and then at a later time to pump the sodium-laden DSR infusate and osmotic ultrafiltrate from peritoneal cavity 11 into bladder 13 via catheters 23 and 25. Specifically, first pump connector 24 of implantable device 20 comprises a first valve 49' to which catheter 25 is connected and a second valve 49 to which catheter 46' is connected. Second pump connecter 22 of implantable device 20 is directly connected to catheter 23. During pumping operations, implantable device 20 controls valves 49 and 49' so as to prevent fluid from being inadvertently pumped from the bladder into the peritoneal cavity or from the peritoneal cavity into the reservoir. For example, to pump fluid into the peritoneal cavity 11 from reservoir 45, implantable device 20 may close off fluidic communication to catheter 25 by appropriately actuating valve 49', may open fluidic communication between catheters 46' and 23 by appropriately actuating valve 49, and may turn in a first direction so as to pump fluid from reservoir 45 via catheters 46' and 23. Reservoir 45 may alternatively be implanted inside the patient's body and connected to the exterior environment using a catheter to permit reservoir 45 to be refilled.

After the DSR infusate has dwelled in the peritoneal cavity for a predetermined amount of time, implantable device 20 may pump that DSR infusate and the osmotic ultrafiltrate to the patient's bladder 13 by closing off communication to catheter 46' by appropriately actuating valve 49 and opening communication to catheter 25 by appropriately actuating valve 49' and turning in a second direction (opposite from the first) so as to pump the fluid into bladder 13 via catheters 23 and 25. It should be appreciated that the functionalities of valves 49 and 49' may be provided by any desired number of valves that are disposed appropriately along catheters 23, 25, and 46' and are controllably actuated by implantable device 20, e.g., via valve controller 86 illustrated in FIG. 4. In certain configurations, the use of one or more passive valves (not controlled by implantable device 20) may be appropriate, e.g., valve 49' may be a passive check valve disposed along catheter 25 that inhibits fluid to flow from the bladder to device 20.

Methods of using the exemplary implantable systems, such as illustrated in FIGS. 1A-1C, is now described with reference to FIG. 1D. Method 1000 includes introducing no or low sodium DSR infusate to the peritoneal cavity from a reservoir that is internal or external to the patient's body (step 1010). For example, as described above with reference to FIG. 1B, the DSR infusate may be introduced using an external pump or gravity. Or, as described above with reference to FIG. 1C, the DSR infusate may be introduced using implantable device 20 and one or more valves in communication therewith. A sufficient amount of DSR infusate is introduced into the peritoneal cavity of the patient and allowed to dwell, to remove sodium from the patient's body into the peritoneal cavity and to cause the osmotic ultrafiltrate to accumulate in the peritoneal cavity, from where it is removed to the bladder.

Sodium is moved from the patient's body via the peritoneal membrane into the peritoneal cavity, from where it is removed to the bladder. This reduces the level of sodium in the body resulting in the elimination of fluid by i) the functioning kidneys through urination and ii) removal to the bladder of the osmotic ultrafiltrate that accumulates in the peritoneal cavity, restoring the serum sodium concentration and reducing the patient's volume of fluid (step 1020). The sodium-laden DSR infusate and osmotic ultrafiltrate is pumped from the peritoneal cavity to the bladder with the implantable device (step 1030). Such pumping may occur after the DSR infusate has been in the peritoneal cavity for a sufficient amount of time to draw a sufficient amount of sodium out of the body to alleviate the fluid overload as described above. Kidneys of the patient also may then excrete fluid through urination, thereby restoring serum sodium concentration (step 1040).

Energy may be wirelessly transferred to the implantable device, and data received from the device, using a charging and communication system such as described above with reference to FIG. 1A (step 1050). For example, the implantable device may record parameters reflective of the health of the patient and the operation of the device, which parameters may be communicated to the charging and communication system. The data, e.g., parameters recorded by the implantable device, then is provided to monitoring and control software, which is in communication with the charging and communication system and is under the control of the treating physician (step 1060). Based on those parameters, the health of the patient may be assessed using the software, and the physician may remotely communicate any modifications to the flow rate, volume, time duration, or frequency with which the implantable device is to deliver the DSR infusate to the peritoneal cavity before removing the DSR infusate and the osmotic ultrafiltrate, containing the extracted sodium, to the bladder (step 1070). Such communication may be performed via the charging and communication system.

Further details of selected components of the exemplary system of FIGS. 1A-1C to practice the inventive methods are now provided with reference to FIGS. 2A-8.

Peritoneal and Bladder Catheters

Figure 2A:
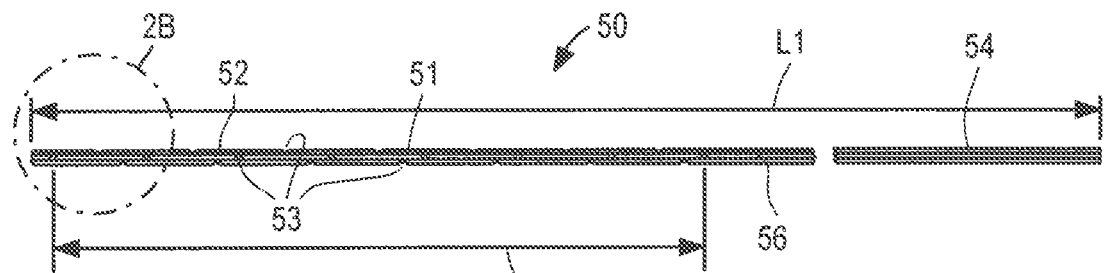
FIGS. 2A and 2B are, respectively, side view and perspective detailed views of an exemplary embodiment of a peritoneal catheter suitable for use with system of FIG. 1, in which FIG. 2B corresponds to detail region 2B of FIG. 2A.
Figure 2B:
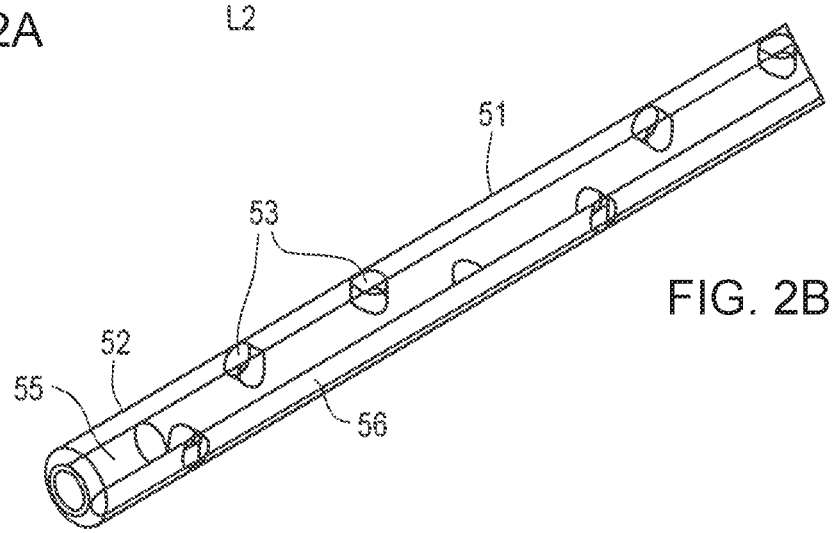

Referring to FIGS. 2A and 2B, peritoneal catheter 50 may be Medionics International Inc.'s peritoneal dialysis Catheter, Model No. PSNA-100 or a catheter having similar structure and functionality. Peritoneal catheter 50 corresponds to peritoneal catheter 23 of FIGS. 1A-1C, and may comprise tube 51 of medical-grade silicone including inlet (distal) end 52 having a plurality of through-wall holes 53 and outlet (proximal) end 54. Holes 53 may be arranged circumferentially offset by about 90 degrees, as shown in FIG. 2B. Peritoneal catheter 50 may also include a polyester cuff (not shown) in the region away from holes 53, to promote adhesion of the catheter to the surrounding tissue, thereby anchoring it in place. Alternatively, inlet end 52 of peritoneal catheter 50 may have a spiral configuration, and an atraumatic tip, with holes 53 distributed over a length of the tubing to reduce the risk of clogging.

Inlet end 52 also may include a polyester cuff to promote adhesion of the catheter to an adjacent tissue wall, thereby ensuring that the inlet end of the catheter remains in position. Outlet end 54 also may include a connector for securing the outlet end of the peritoneal catheter to implantable device 20. In one preferred embodiment, the distal end of the peritoneal catheter, up to the ingrowth cuff, may be configured to pass through a conventional 16F peel-away sheath. In addition, the length of the peritoneal catheter may be selected to ensure that it lies along the bottom of the body cavity, and is sufficiently resistant to torsional motion so as not to become twisted or kinked during or after implantation.

Figure 3A:
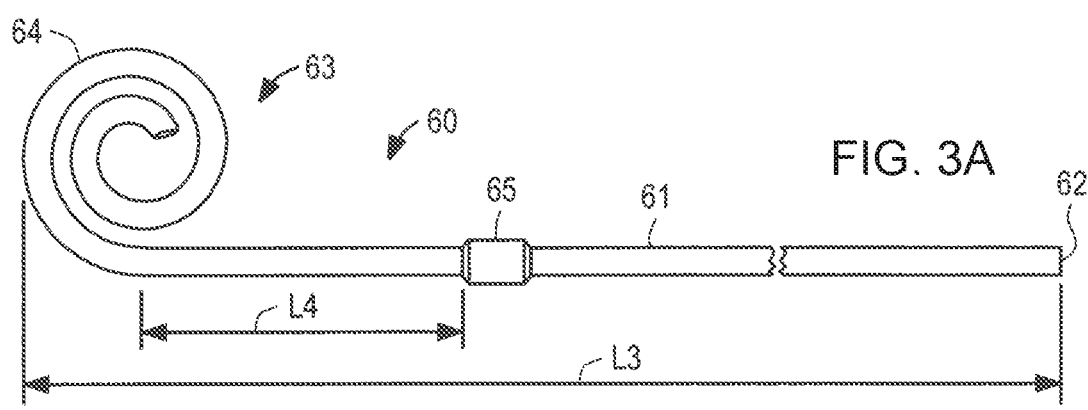
FIGS. 3A and 3B are, respectively, side and perspective views, respectively, of first and second embodiments of bladder catheters suitable for use with the system of FIG. 1.

With respect to FIG. 3A, a first embodiment of bladder catheter 60 is described, corresponding to bladder catheter 25 of FIGS. 1A-1C. Bladder catheter 60 preferably comprises tube 61 of medical-grade silicone having inlet (proximal) end 62 and outlet (distal) end 63 including spiral structure 64, and polyester ingrowth cuff 65. Bladder catheter 60 includes a single internal lumen that extends from inlet end 62 to a single outlet at the tip of spiral structure 64, commonly referred to as a "pigtail" design. Inlet end 62 may include a connector for securing the inlet end of the bladder catheter to implantable device 20, or may have a length that can be trimmed to fit a particular patient. In one embodiment, bladder catheter 60 may have length L3 of about 45 cm, with cuff 65 placed length L4 of about 5 to 6 cm from spiral structure 64. Bladder catheter 60 may be loaded onto a stylet with spiral structure 64 straightened, and implanted using a minimally invasive technique in which outlet end 63 and spiral structure 64 are passed through the wall of a patient's bladder using the stylet. When the stylet is removed, spiral structure 64 returns to the coiled shape shown in FIG. 3A. Once outlet end 63 of bladder catheter 60 is disposed within the patient's bladder, the remainder of the catheter is implanted using a tunneling technique, such that inlet end 62 of the catheter may be coupled to implantable device 20. Spiral structure 64 may reduce the risk that outlet end 63 accidentally will be pulled out of the bladder before the tissue surrounding the bladder heals sufficiently to incorporate ingrowth cuff 65, thereby anchoring the bladder catheter in place.

In a preferred embodiment, bladder catheter 60 is configured to pass through a conventional peel-away sheath. Bladder catheter 60 preferably is sufficiently resistant to torsional motion so as not to become twisted or kinked during or after implantation. In a preferred embodiment, peritoneal catheter 50 and bladder catheter 60 preferably are different colors, have different exterior shapes (e.g., square and round) or have different connection characteristics so that they cannot be inadvertently interchanged during connection to implantable device 20. Optionally, bladder catheter 60 may include an internal duckbill valve positioned midway between inlet 62 and outlet end 63 of the catheter to ensure that urine does not flow from the bladder into the peritoneal cavity if the bladder catheter is accidentally pulled free from the pump connector of implantable device 20 and/or if the pump of implantable device 20 is actuated so as to draw the DSR infusate from reservoir 45 into the patient's peritoneal cavity.

In an alternative embodiment, the peritoneal and bladder catheters devices may incorporate one or several anti-infective agents to inhibit the spread of infection between body cavities. Examples of anti-infective agents which may be utilized may include, e.g., bacteriostatic materials, bactericidal materials, one or more antibiotic dispensers, antibiotic eluting materials, and coatings that prevent bacterial adhesion, and combinations thereof. Additionally, implantable device 20 may include a UV lamp configured to irradiate fluid in the peritoneal and/or bladder catheters so as to kill any pathogens that may be present and thus inhibit the development of infection, as described further below with respect to FIGS. 4 and 5B.

Alternatively, rather than comprising separate catheters, peritoneal and bladder catheters 50, 60 may share a common wall, which may be convenient because the bladder and peritoneal cavity share a common wall, thereby facilitating insertion of a single dual-lumen tube. In addition, either or both of the peritoneal or bladder catheters may be reinforced along a portion of its length or along its entire length using ribbon or wire braiding or lengths of wire or ribbon embedded or integrated within or along the catheters. The braiding or wire may be fabricated from metals such as stainless steels, superelastic metals such as nitinol, or from a variety of suitable polymers. Such reinforcement may also be used for catheter 46 connected to optional reservoir 45.

Figure 3B:
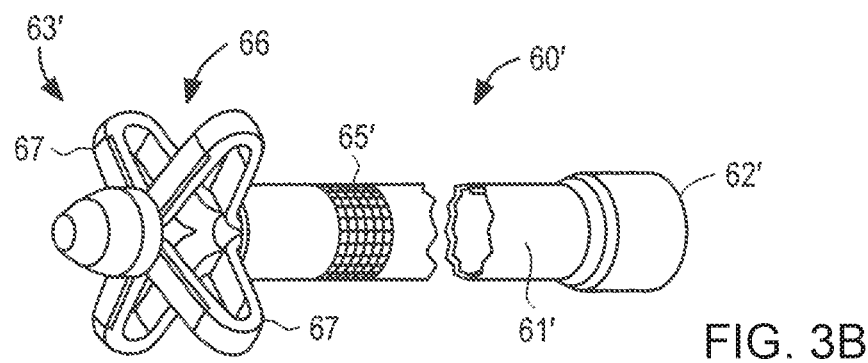

With respect to FIG. 3B, a second embodiment of a bladder catheter is described, in which similar components are identified with like-primed numbers. Bladder catheter 60' preferably comprises tube 61' of medical-grade silicone having inlet end 62', outlet end 63' and polyester ingrowth cuff 65'. In accordance with this embodiment, outlet end 63' includes malecot structure 66, illustratively comprising four resilient wings 67 that expand laterally away from the axis of the catheter to reduce the risk that outlet end 63' of the catheter will be inadvertently pulled loose after placement. Inlet end 62' may include a connector for securing the inlet end of the bladder catheter to implantable device 20, or may have a length that can be trimmed to fit a particular patient.

Malecot structure 66 preferably is constructed so that wings 67 deform to a substantially flattened configuration when a stylet is inserted through the lumen of the catheter. In this manner, bladder catheter 60' may be loaded onto a stylet, and using a minimally invasive technique, outlet end 63' and malecot structure 66 may be passed through the wall of a patient's bladder using the stylet. When the stylet is removed, wings 67 of the malecot structure return to the expanded shape shown in FIG. 3B. Once outlet end 63' of bladder catheter 60' is coupled to the patient's bladder, the remainder of the catheter is implanted using a tunneling technique, such that inlet end 62' of the catheter may be coupled to implantable device 20. Malecot structure 66 may reduce the risk that outlet end 63' accidentally will be pulled out of the bladder before the tissue surrounding the bladder heals sufficiently to incorporate ingrowth cuff 65'. As for the embodiment of FIG. 3A, the bladder catheter of FIG. 3B may be configured to pass through a conventional peel-away sheath, and preferably is sufficiently resistant to torsional motion so as not to become twisted or kinked during or after implantation.

The Implantable Device

Figure 4:
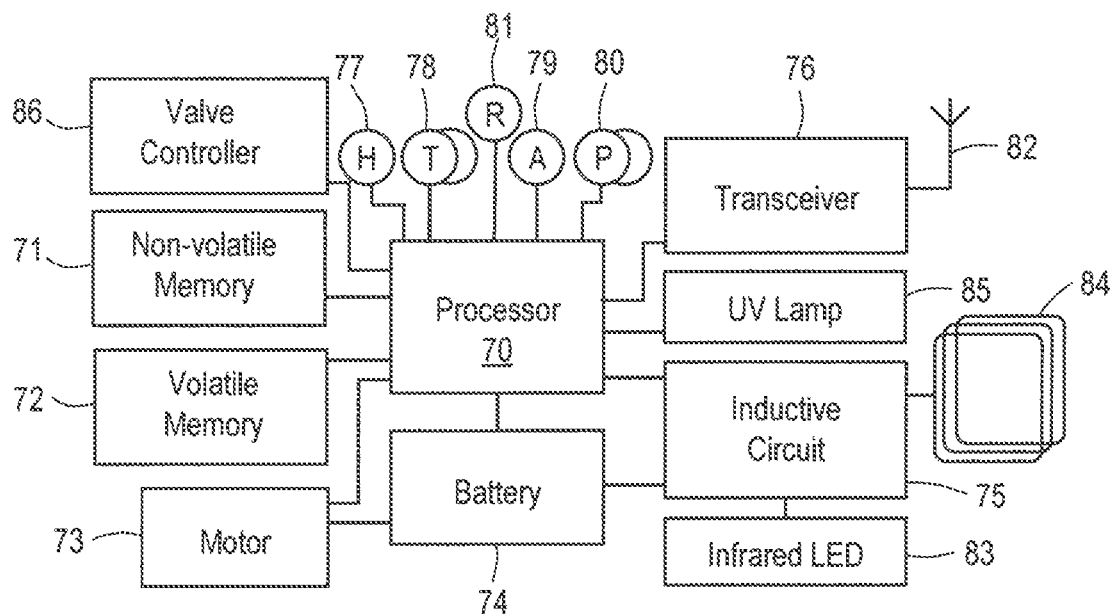
FIG. 4 is a schematic diagram of the electronic components of an exemplary embodiment of the implantable device.
Figures 5A, 5B:
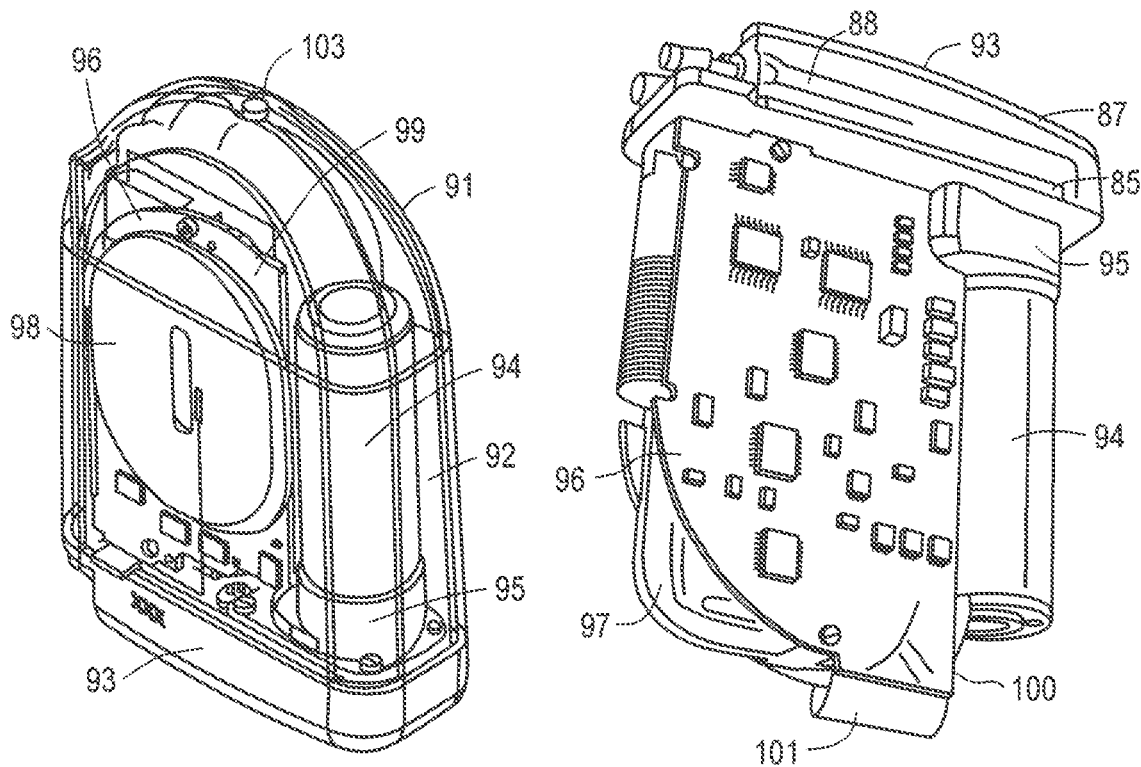
FIGS. 5A and 5B are, respectively, a perspective view of the implantable device with the housing shown in outline and a perspective view of the obverse side of the implantable device with the housing and low water permeable filler removed.

Referring now to FIG. 4, a schematic depicting the functional blocks of implantable device 20 suitable for use in practicing the methods of the present invention is described. Implantable device 20 includes control circuitry, illustratively processor 70 coupled to nonvolatile memory 71, such as flash memory or electrically erasable programmable read only memory, and volatile memory 72 via data buses. Processor 70 is electrically coupled to electric motor 73, battery 74, inductive circuit 75, radio transceiver 76, UV lamp 85, and a plurality of sensors, including humidity sensor 77, a plurality of temperature sensors 78, accelerometer 79, a plurality of pressure sensors 80, and respiratory rate sensor 81. Inductive circuit 75 is electrically coupled to coil 84 to receive energy transmitted from charging and communication system 30, while transceiver 76 is coupled to antenna 82, and likewise is configured to communicate with a transceiver in charging and communication system 30, as described below. Optionally, inductive circuit 75 also may be coupled to infrared light emitting diode 83. Motor 73 may include a dedicated controller, which interprets and actuates motor 73 responsive to commands from processor 70. Optionally, processor 70 is further in communication with valve controller 86. All of the components depicted in FIG. 4 are contained within a low volume sealed biocompatible housing, as shown in FIG. 5A.

Processor 70 executes firmware stored in nonvolatile memory 71 which controls operation of motor 73 responsive to signals generated by motor 73, sensors 77-81 and commands received from transceiver 76. Processor 70 also controls reception and transmission of messages via transceiver 76 and operation of inductive circuit 75 to charge battery 74. In addition, processor 70 receives signals generated by Hall Effect sensors located within motor 73, which are used to compute direction and revolutions of the gears of the gear pump, and thus fluid volume pumped and the viscosity of that fluid, as described below. Processor 70 preferably includes a low-power mode of operation and includes an internal clock, such that the processor can be periodically awakened to handle pumping, pump tick mode, or communications and charging functions, and/or awakened to handle commands received by transceiver 76 from handpiece 32. In one embodiment, processor 70 comprises a member of the MSP430 family of microcontroller units available from Texas Instruments, Incorporated, Dallas, Tex., and may incorporate the nonvolatile memory, volatile memory, and radio transceiver components depicted in FIG. 4. In addition, the firmware executed on processor 70 may be configured to respond directly to commands sent to implantable device 20 via charging and communication system 30. Processor 70 also is configured to monitor operation of motor 72 (and any associated motor controller) and sensors 77-81, as described below, and to store data reflecting operation of the implantable device, including event logs and alarms. Thus, data is reported to the charging and communication system when it is next wirelessly coupled to the implantable device. In a preferred embodiment, processor 70 generates up to eighty log entries per second prior to activating the pump, about eight log entries per second when the implantable system is actively pumping and about one log entry per hour when not pumping.

Nonvolatile memory 71 preferably comprises flash memory or EEPROM, and stores a unique device identifier for implantable device 20, firmware to be executed on processor 70, configuration set point data relating to operation of the implantable device, and optionally, coding to be executed on transceiver 76 and/or inductive circuit 75, and a separate motor controller, if present. Firmware and set point data stored on nonvolatile memory 71 may be updated using new instructions provided by control and monitoring system 40 via charging and communication system 30. Volatile memory 72 is coupled to and supports operation of processor 70, and stores data and event log information gathered during operation of implantable device 20. Volatile memory 72 also serves as a buffer for communications sent to, and received from, charging and communication system 30.

Transceiver 76 preferably comprises a radio frequency transceiver and is configured for bi-directional communications via antenna 76 with a similar transceiver circuit disposed in handpiece 32 of charging and communication system 30. Transceiver 76 also may include a low power mode of operation, such that it periodically awakens to listen for incoming messages and responds only to those messages including the unique device identifier assigned to that implantable device. Alternatively, because transceiver 76 communicates only with the corresponding transceiver in handpiece 32 of its associated charging and communication system 30, transceiver 76 may be configured to send or receive data only when inductive circuit 75 of the implantable device is active. In addition, transceiver 76 may employ an encryption routine to ensure that messages sent from, or received by, the implantable device cannot be intercepted or forged.

Inductive circuit 75 is coupled to coil 84, and is configured to recharge battery 74 of the implantable device when exposed to a magnetic field supplied by a corresponding inductive circuit within handpiece 32 of charging and communication system 30. In one embodiment, inductive circuit 75 is coupled to optional infrared LED 83 that emits an infrared signal when inductive circuit 75 is active. The infrared signal may be received by handpiece 32 of charging and communication system 30 to assist in locating the handpiece relative to the implantable device, thereby improving the magnetic coupling and energy transmission to the implantable device.

Inductive circuit 75 optionally may be configured not only to recharge battery 74, but to directly provide energy to motor 73 in a "boost" mode or jog/shake mode to unblock the pump. In particular, if processor 70 detects that motor 73 is stalled, e.g., due to a block created by fibrin or other debris in the peritoneal cavity, an alarm may be stored in memory. When implantable device 20 next communicates with charging and communication system 30, the alarm is reported to handpiece 32, and the patient may be given the option of depressing multifunction button 34 to apply an overvoltage to motor 73 from inductive circuit 75 for a predetermined time period to free the pump blockage. Alternatively, depressing the multi-function button may cause processor 70 to execute a set of commands by which motor 73 is jogged or shaken, e.g., by alternatingly running the motor is reverse and then forward, to disrupt the blockage. Because such modes of operation may employ higher energy consumption than expected during normal operation, it is advantageous to drive the motor during such procedures with energy supplied via inductive circuit 75.

Battery 74 preferably comprises a lithium ion or lithium polymer battery capable of long lasting operation, e.g., up to three years, when implanted in a human, so as to minimize the need for re-operations to replace implantable device 20. In one preferred embodiment, battery 74 supplies a nominal voltage of 3.6V, a capacity of 150 mAh when new, and a capacity of about 120 mAh after two years of use. Preferably, battery 74 is configured to supply a current of 280 mA to motor 73 when pumping; 25 mA when the transceiver is communicating with charging and communication system 30; 8 mA when processor 70 and related circuitry is active, but not pumping or communicating; and 0.3 mA when the implantable device is in low power mode. More preferably, battery 74 should be sized to permit a minimum current of at least 450 mAh for a period of 10 seconds and 1 A for 25 milliseconds during each charging cycle.

Motor 73 preferably is a brushless direct current or electronically commuted motor having a splined output shaft that drives a set of floating gears that operate as a gear pump, as described below. Motor 73 may include a dedicated motor controller, separate from processor 70, for controlling operation of the motor. Motor 73 may include a plurality of Hall Effect sensors, preferably two or more, for determining motor position and direction of rotation. Due to the high humidity that may be encountered in implantable device 20, processor 70 may include programming to operate motor 73, although with reduced accuracy, even if some or all of the Hall Effect sensors fail.

In a preferred embodiment, motor 73 is capable of driving the gear pump to generate a nominal flow rate of 150 ml/min and applying a torque of about 1 mNm against a pressure head of 30 cm water at 3000 RPM. In this embodiment, the motor preferably is selected to drive the gears at from 1000 to 5000 RPM, corresponding to flow rates of from 50 to 260 ml/min, respectively. The motor preferably has a stall torque of at least 3 mNm at 500 mA at 3 V, and more preferably 6 mNm in order to crush non-solid proteinaceous materials. As discussed above, the motor preferably also supports a boost mode of operation, e.g., at 5 V, when powered directly through inductive circuit 75. Motor 73 preferably also is capable of being driven in reverse as part of a jogging or shaking procedure to unblock the gear pump.

Processor 70 may be programmed to automatically and periodically wake up and enter a pump tick mode. In this mode of operation, the gear pump is advanced slightly, e.g., about 120 degrees as measured by the Hall Effect sensors, before processor 70 returns to low power mode. Preferably, this interval is about every 20 minutes, although it may be adjusted by the physician using the monitoring and control system. This pump tick mode is expected to prevent the DSR infusate and the osmotic ultrafiltrate from partially solidifying, and blocking the gear pump.

In addition, processor 70 also may be programmed to enter a jog or shake mode when operating on battery power alone, to unblock the gear pump. Similar to the boost mode available when charging the implantable device with the handpiece of charging and communication system 30, the jog or shake mode causes the motor to rapidly alternate the gears between forward and reverse directions to crush or loosen any buildup of tissue or other debris in the gear pump or elsewhere in the fluid path. Specifically, in this mode of operation, if the motor does not start to turn within a certain time period after it is energized (e.g., 1 second), the direction of the motion is reversed for a short period of time and then reversed again to let the motor turn in the desired direction. If the motor does still not turn (e.g., because the gear pump is jammed) the direction is again reversed for a period of time (e.g., another 10 msec). If the motor still is not able to advance the time interval between reversals of the motor direction is reduced to allow for the motor to develop more power, resulting in a shaking motion of the gears. If the motor does not turn forward for more than 4 seconds, the jog mode of operation is stopped, and an alarm is written to the event log. If the motor was unable to turn forward, processor 70 will introduce a backwards tick before the next scheduled fluid movement. A backward tick is the same as a tick (e.g., about 120 degrees forward movement of the motor shaft) but in the reverse direction, and is intended to force the motor backwards before turning forward, which should allow the motor to gain momentum.

Sensors 77-81 continually monitor humidity, temperature, acceleration, pressure, and respiratory rate, and provide corresponding signals to processor 70 which stores the corresponding data in memory 71 for later transmission to monitoring and control system 40. In particular, humidity sensor 77 is arranged to measure humidity within the housing of the implantable device, to ensure that the components of implantable device are operated within expected operational limits. Humidity sensor 77 preferably is capable of sensing and reporting humidity within a range or 20% to 100% with high accuracy. One or more of temperature sensors 78 may be disposed within the housing and monitor the temperature of the implantable device, and in particular battery 74 to ensure that the battery does not overheat during charging, while another one or more of temperature sensors 78 may be disposed so as to contact fluid entering at inlet 62 and thus monitor the temperature of the fluid, e.g., for use in assessing the patient's health. Accelerometer 79 is arranged to measure acceleration of the implant, preferably along at least two axes, to detect periods of activity and inactivity, e.g., to determine whether the patient is sleeping or to determine whether and when the patient is active. This information is provided to processor 70 to ensure that the pump is not operated when the patient is indisposed to attend to voiding of the bladder.

Implantable device 20 preferably includes multiple pressure sensors 80, which are continually monitored during waking periods of the processor. As described below with respect to FIG. 6A, the implantable device of the present invention preferably includes four pressure sensors: a sensor to measure the pressure in the peritoneal cavity, a sensor to measure the ambient pressure, a sensor to measure the pressure at the outlet of the gear pump, and a sensor to measure the pressure in the bladder. These sensors preferably are configured to measure absolute pressure between 450 mBar and 1300 mBar while consuming less than 50 mW at 3V. Preferably, the sensors that measure pressure at the pump outlet and in the bladder are placed across a duckbill valve, which prevents reverse flow of urine and/or used DSR infusate and/or osmotic ultrafiltrate back into the gear pump and also permits computation of flow rate based on the pressure drop across the duckbill valve.

Respiratory rate monitor 81 is configured to measure the patient's respiratory rate, e.g., for use in assessing the patient's health. Alternatively, the patient's respiratory rate may be measured based on the outputs of one or more of pressure sensors 80, e.g., based on changes in the ambient pressure or the pressure in the peritoneal cavity caused by the diaphragm periodically compressing that cavity during breathing.

Any desired number of additional sensors for measuring the health of the patient may also be provided in operable communication with processor 70 and may output recordable parameters for storage in memory 71 and transmission to monitoring and control system 40, that the physician may use to assess the patient's health. For example, chemical or biochemical sensors may be provided that are configured to monitor the composition and/or sodium concentration of the sodium-laden DSR infusate and osmotic ultrafiltrate.

Processor 70 preferably is programmed to pump a predetermined volume of fluid from the peritoneal cavity to the bladder after that fluid has been in the peritoneal cavity for a predetermined amount of time and with a predetermined frequency. Such volume, time, and frequency preferably are selected to optimize sodium removal to maintain or improve the patient's health and to alleviate the fluid overload. The volume, time, and frequency may be selected based on the patient's symptoms, the activity and habits of the patient, the permeability of the peritoneal membrane and the osmotic characteristics of the DSR infusate. For example, the physician may initially program processor 70 with a first time, volume, and frequency based on his perception of the patient's health and habits, and later may adjust that initial programming to vary the volume, time, and/or frequency based on his perception of changes in the patient's health, for example based on changes over time in parameters measured by implantable device 20 and relayed to the physician via monitoring and control software 40.

Processor 70 also may be programmed to monitor the sensors 77-81 and to generate an alert condition that is relayed to the clinician indicative of a potential decline in the patient's health. For example, processor 70 may monitor pressure sensors 80 to determine whether, over predetermined time intervals, there is an increase in pressure within the peritoneal cavity. Such pressure increases may be the result of an increase in the rate of accumulation of fluid in the peritoneal cavity, which may in turn indicate heart failure decompensation. Such an alert may result in the patient being directed to seek immediate treatment and arrest such decompensation.

In other embodiments, processor 70 may be programmed to pump fluid from the peritoneal cavity to the bladder only when the pressure in the peritoneal cavity exceeds a first predetermined value, and the pressure in the bladder is less than a second predetermined value, so that the bladder does not become overfull. To account for patient travel from a location at sea level to a higher altitude, the ambient pressure measurement may be used to calculate a differential value for the peritoneal pressure. In this way, the predetermined pressure at which the pump begins operation may be reduced, to account for lower atmospheric pressure. Likewise, the ambient pressure may be used to adjust the predetermined value for bladder pressure. In this way, the threshold pressure at which the pumping ceases may be reduced, because the patient may experience bladder discomfort at a lower pressure when at a high altitude location.

Further, processor 70 may be programmed to include a timer that monitors the elapsed time from when the DSR infusate was pumped from the reservoir to the patient's peritoneal cavity, and after expiration of a predetermined or patient-settable dwell time, to pump the sodium-laden DSR infusate and osmotic ultrafiltrate from the peritoneal cavity to the patient's bladder. Such timer programming also may include an override feature, such that a parameter measured by sensors 77-81, such as excess pressure in the peritoneal cavity, may trigger transfer of the contents of the peritoneal cavity to the bladder prior to expiration of a designated dwell time.

Optionally, controller 70 is in operable communication with UV lamp 85, which is configured to irradiate and thus kill pathogens in the DSR infusate both before and after fluid is provided to or extracted from the peritoneal cavity. UV lamp 85 preferably generates light in the UV-C spectral range (about 200-280 nm), particularly in the range of about 250-265 nm, which is also referred to as the "germicidal spectrum" because light in that spectral range breaks down nucleic acids in the DNA of microorganisms. Low-pressure mercury lamps have an emission peak at approximately 253.7 nm, and may suitably be used for UV lamp 85. Alternatively, UV lamp 85 may be a UV light emitting diode (LED), which may be based on AlGaAs or GaN.

Under the control of controller 70, UV lamp 85 irradiates any fluid passing through the implantable device for a preselected amount of time sufficient to kill pathogens that may be present in that fluid. Specifically, the flow rate of the fluid through the device may be selected (e.g., pre-programmed) so as to irradiate the fluid with a sufficient dosage of UV light to inhibit the growth of colonies of pathogens. For example, it is known that dosages of 253.7 nm UV light of between about 5,500-7,000 $\mu$Ws/cm$^2$ are sufficient to provide 100% kill rates for many organisms, including *E. coli, Proteus* spp., *Klebsiella* spp., *Serratia* spp., *Leptospirosis* spp., *Staphylococcus haemolyticus*, and Enterococci. Higher dosages, e.g., between about 8,500-12,000 $\mu$Ws/cm$^2$, may be required to provide 100% kill rates for other organisms, including *Kliebsiella* ssp., *Enterobacter* spp., *Psuedomonas* spp., and *Neisseria gonorrhoeae*. However, the dosage to sufficiently inhibit colony growth may be lower. For example, *E. coli* requires only 3000 $\mu$Ws/cm$^2$ to inhibit growth, whereas 6,600 µWs/cm² may be needed to provide a 100% kill rate. Controller 70 may be pre-programmed to set a flow rate of fluid through the tubing sufficient to inhibit colony growth of one or more target pathogens based on the intensity of UV lamp 85, the reflective conditions within the portion of the housing in which UV lamp 85 is used (e.g., upper portion 93 described below with reference to FIG. 5B), the configuration of the tubing being exposed to the UV lamp, the distance between the tubing and the UV lamp, and the susceptibility of target pathogens to the spectrum emitted by UV lamp 85.

Still referring to FIG. 4, in some embodiments processor 70 also may be in communication with valve controller 86; alternatively, valve controller 86 may be part of the functionality of processor 70. Valve controller 86 controls the actuation of any valves that may be used to control the flow of DSR infusate between the reservoir, the peritoneal cavity, and the bladder. For example, as described above with reference to FIG. 1C, implantable device 20 may be configured to pump the DSR infusate from an external or internal reservoir to the peritoneal cavity, while actuating valves 49 and 49' so as to close fluidic access to the bladder and thus avoid inadvertently pumping fluid from the bladder into the peritoneal cavity; and may be configured to pump fluid from the peritoneal cavity to the bladder, while actuating valves 49 and 49' so as to close fluidic access to the reservoir and thus avoid inadvertently pumping fluid from the peritoneal cavity into the reservoir. Valve controller 86 may coordinate the actuation of valves 49 and 49' in such a manner, or in any other appropriate manner based on the particular valve configuration.

Referring now to FIGS. 5A and 5B, further details of an exemplary embodiment of implantable device 90 are provided. In FIG. 5A, housing 91 is shown as transparent, although it should of course be understood that housing 91 comprises an opaque biocompatible plastic, glass and/or metal alloy materials. In FIG. 5B, the implantable device is shown with lower portion 92 of housing 91 removed from upper housing 93 and without a glass bead/epoxy filler material that is used to prevent moisture from accumulating in the device. In FIGS. 5A and 5B, motor 94 is coupled to gear pump housing 95, which is described in greater detail with respect to FIG. 6. The electronic components discussed above with respect to FIG. 4 are disposed on circuit board substrate 96, which extends around and is fastened to support member 97. Coil 98 (corresponding to coil 84 of FIG. 4) is disposed on flap 99 of the substrate and is coupled to the electronic components on flap 100 by flexible cable portion 101. Support member 97 is fastened to upper housing 93 and provides a cavity that holds battery 102 (corresponding to battery 74 of FIG. 4). Lower portion 92 of housing 91 includes port 103 for injecting the glass bead/epoxy mixture after upper portion 93 and lower portion 92 of housing 91 are fastened together, to reduce space in the housing in which moisture can accumulate.

Housing 91 also may include features designed to reduce movement of the implantable pump once implanted within a patient, such as a suture hole to securely anchor the implantable device to the surrounding tissue. Housing 91 may in addition include a polyester ingrowth patch that facilitates attachment of the implantable device to the surrounding tissue following subcutaneous implantation.

Additionally, the implantable device optionally may incorporate anti-clogging agents, such enzyme eluting materials that specifically target the proteinaceous components of fluid from the peritoneal cavity, enzyme eluting materials that specifically target the proteinaceous and encrustation promoting components of urine, chemical eluting surfaces, coatings that prevent adhesion of proteinaceous compounds, and combinations thereof. Such agents, if provided, may be integrated within or coated upon the surfaces of the various components of the system.

Referring to FIG. 5B, upper housing 93 optionally includes UV lamp 85. Within upper housing 93, the fluid channels 88 for conducting the fluid may extend approximately linearly, or alternatively may include one or more curves or bends so as to increase the volume of fluid that may be simultaneously exposed UV lamp 86, and thus allow for an increase in the flow rate. For example, the fluid channels 88 may include an approximate spiral, an approximate sine wave, or an approximate "S" curve so as to increase the volume of fluid that may be simultaneously exposed to UV lamp 86. Upper housing 93 further may include reflective coating 87, e.g., a white coating such as ZnO or other diffuse or Lambertian reflector, so as to enhance irradiation of the tubing and shield the patient from potential UV light exposure.

Figure 6B:
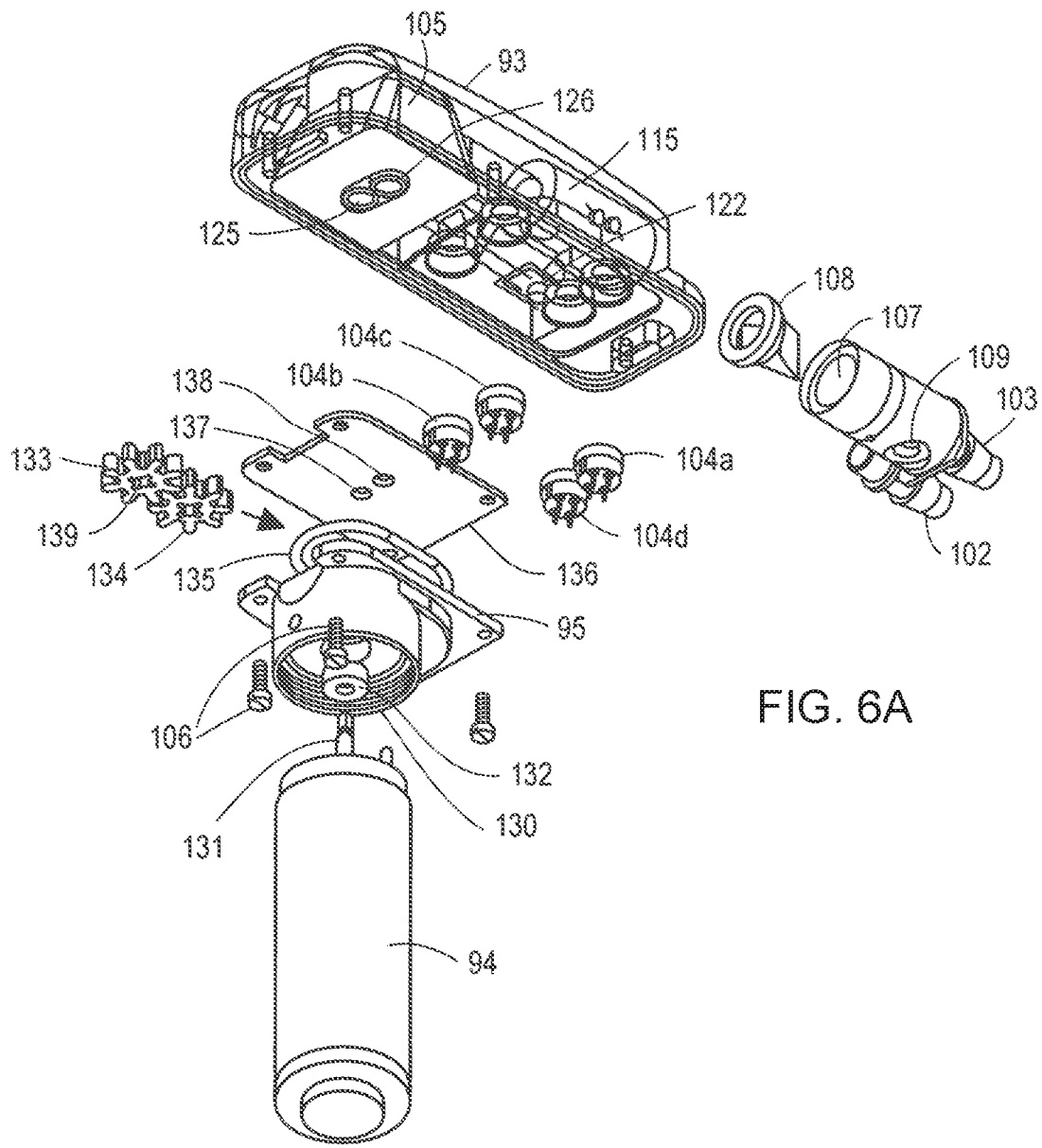
Figure 6B:
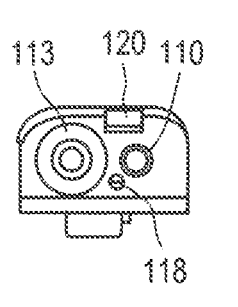

Referring now to FIGS. 6A to 6D, further details of the gear pump and fluid path are described. In FIGS. 6A-6D, like components are identified using the same reference numbers from FIGS. 5A and 5B. FIG. 6A is an exploded view showing assembly of motor 94 with gear pump housing 95 and upper housing 93, as well as the components of the fluid path within the implantable device. Upper housing 93 preferably comprises a high strength plastic or metal alloy material that can be molded or machined to include openings and channels to accommodate inlet nipple 102, outlet nipple 103, pressure sensors 104*a*-104*d*, manifold 105 and screws 106. Nipples 102 and 103 preferably are machined from a high strength biocompatible metal alloy, and outlet nipple 103 further includes channel 107 that accepts elastomeric duckbill valve 108. Outlet nipple 103 further includes lateral recess 109 that accepts pressure sensor 104*a*, which is arranged to measure pressure at the inlet end of the bladder catheter, corresponding to pressure in the patient's bladder (or peritoneal cavity).

Figure 6C:
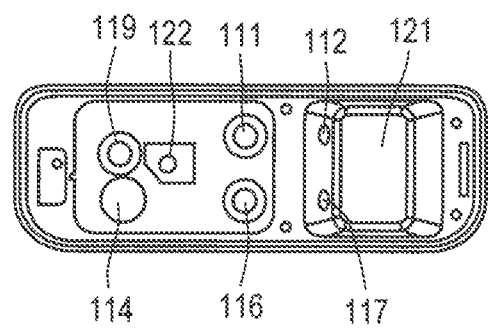
Figure 6D:
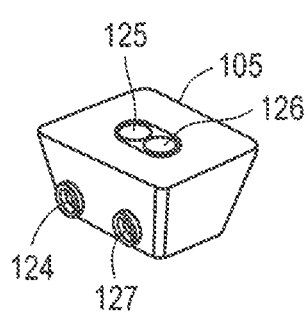

Referring now also to FIGS. 6B and 6C, inlet nipple 102 is disposed within opening 110, which forms a channel in upper housing 93 that includes opening 111 for pressure sensor 104*b* and opening 112 that couples to manifold 105. Pressure sensor 104*b* is arranged to measure the pressure at the outlet end of the peritoneal catheter, corresponding to pressure in the peritoneal cavity. Outlet nipple 103, including duckbill valve 107, is disposed within opening 113 of upper housing 93 so that lateral recess 108 is aligned with opening 114 to permit access to the electrical contacts of pressure sensor 104*a*. Opening 113 forms channel 115 that includes opening 116 for pressure sensor 104*c*, and opening 117 that couples to manifold 105. Upper housing 93 preferably further includes opening 118 that forms a channel including opening 119 for accepting pressure sensor 104*d*. Pressure sensor 104*d* measures ambient pressure, and the output of this sensor is used to calculate differential pressures as described above. Upper housing further includes notch 120 for accepting connector 26 (see FIG. 1A) for retaining the peritoneal and bladder catheters coupled to inlet and outlet nipples 102 and 103. Upper housing 93 further includes recess 121 to accept manifold 105, and peg 122, to which support member 97 (see FIG. 5B) is connected.

Manifold 105 preferably comprises a molded elastomeric component having two separate fluid channels (such channels designated 88 in FIG. 5B) that couple inlet and outlet flow paths through upper housing 93 to the gear pump. The first channel includes inlet 124 and outlet 125, while the second channel includes inlet 126 and outlet 127. Inlet 124 couples to opening 112 (see FIG. 6C) of the peritoneal path and outlet 127 couples to opening 117 of the bladder path. Manifold 105 is configured to improve manufacturability of the implantable device, by simplifying construction of upper housing 93 and obviating the need to either cast or machine components with complicated non-linear flow paths. Optional UV lamp 86 and surface 87 (not shown in FIGS. 6A-6D) may be placed in suitable positions within housing 93 and relative to manifold 105 to sufficiently irradiate the fluid as motor 94 pumps the fluid through housing 93.

Motor 94 is coupled to gear pump housing 95 using mating threads 130, such that splined shaft 131 of motor 94 passes through bearing 132. The gear pump of the present invention comprises intermeshing gears 133 and 134 enclosed in gear pump housing 95 by O-ring seal 135 and plate 136. The gear pump is self-priming. Plate 136 includes openings 137 and 138 that mate with outlet 125 and inlet 126 of manifold 105, respectively. Splined shaft 131 of motor 94 extends into opening 139 of gear 133 to provide floating engagement with that gear.

The Charging and Communication System

Figure 7A:
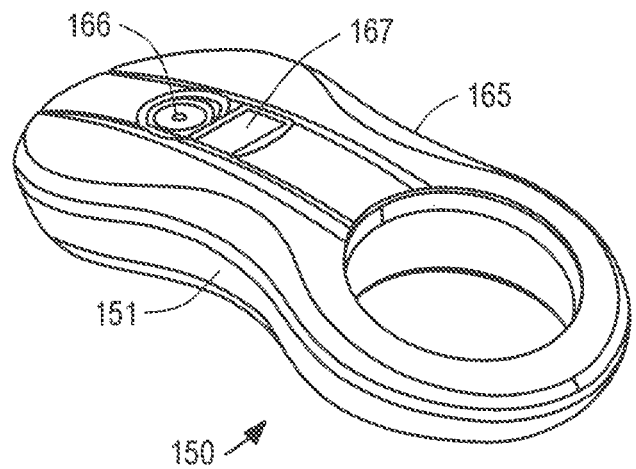
FIGS. 7A and 7B are, respectively, perspective and top views of the handpiece portion of an exemplary charging and communication system for use in practicing the methods of the present invention.
Figure 7B:
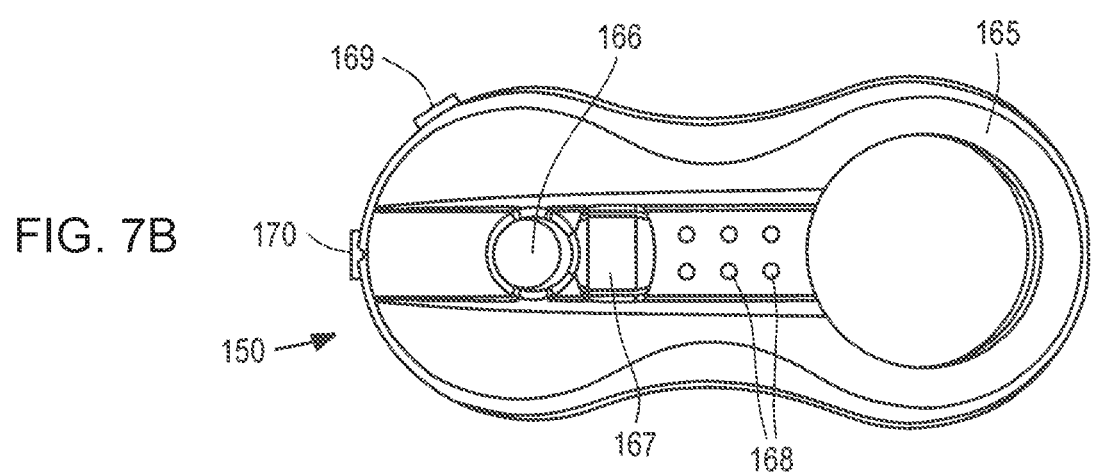
Figure 8:
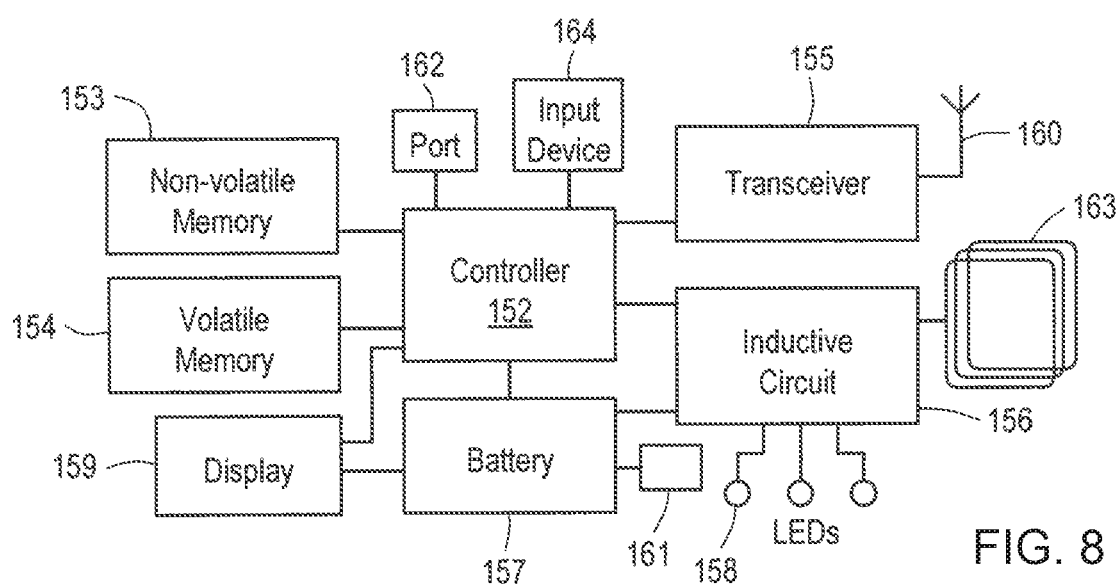
FIG. 8 is a schematic diagram of the electronic components of an exemplary embodiment of the charging and communication system for use in practicing the methods of the present invention.

Referring to FIGS. 7A, 7B and 8, charging and communication system 150 (corresponding to system 30 of FIG. 1A) is described in greater detail. In one preferred embodiment, charging and communication system 150 comprises handpiece 151 and base 31 (see FIG. 1A). Base 31 provides comprises a cradle for recharging handpiece 151, and preferably contains a transformer and circuitry for converting conventional 120/220/240V power service to a suitable DC current to charge handpiece 151 when it is coupled to the base. Alternatively, handpiece 151 may include circuitry for charging the handpiece battery, and a detachable power cord. In this embodiment, handpiece 151 may be directly plugged into a wall socket for charging, and the power cord removed when the handpiece is used to recharge the implantable device.

As shown in FIG. 8, handpiece 151 contains controller 152, illustratively the processor of a micro-controller unit coupled to nonvolatile memory 153 (e.g., either EEPROM or flash memory), volatile memory 154, radio transceiver 155, inductive circuit 156, battery 157, indicator 158 and display 159. Controller 152, memories 153 and 154, and radio transceiver 155 may be incorporated into a single microcontroller unit, such as the MPS430 family of microprocessors, available from Texas Instruments Incorporated, Dallas, Tex. Transceiver 155 is coupled to antenna 160 for sending and receiving information to implantable device 20. Battery 157 is coupled to connector 161 that removably couples with a connector in base 31 to recharge the battery. Port 162, such as a USB port or comparable wireless circuit, is coupled to controller 152 to permit information to be exchanged between handpiece 151 and the monitoring and control system. Inductive circuit 156 is coupled to coil 163. Input device 164, preferably a multi-function button, also is coupled to controller 152 to enable a patient to input a limited number of commands. Indicator 158 illustratively comprises a plurality of LEDs that illuminate to indicate the quality of charge coupling achieved between the handpiece and implantable device, and therefore assist in optimizing the positioning of handpiece 151 relative to the implantable device during recharging. In one preferred embodiment, indicator 158 is omitted, and instead a bar indicator provided on display 159 that indicates the quality-of-charging resulting from the coupling of coils 163 and 84.

In a preferred embodiment, handpiece 151 includes a device identifier stored in nonvolatile memory 153 that corresponds to the device identifier stored in nonvolatile memory 71 of the implantable device, such that handpiece 151 will communicate only with its corresponding implantable device 20. Optionally, a configurable handpiece for use in a physician's office may include the ability to interrogate an implantable device to request that device's unique device identifier, and then change the device identifier of the monitoring and control system 40 to that of the patient's implantable device, so as to mimic the patient's handpiece. In this way, a physician may adjust the configuration of the implantable device if the patient forgets to bring his handpiece 151 with him during a visit to the physician's office.

Controller 152 executes firmware stored in nonvolatile memory 153 that controls communications and charging of the implantable device. Controller 152 also is configured to transfer and store data, such as event logs, uploaded to handpiece 151 from the implantable device, for later retransmission to monitoring and control system 40 via port 162, during physician office visits. Alternatively, handpiece 151 may be configured to recognize a designated wireless access point within the physician's office, and to wirelessly communicate with monitoring and control system 40 during office visits. As a further alternative, base 31 may include telephone circuitry for automatically dialing and uploading information stored on handpiece 151 to a physician's website via a secure connection, such as alarm information.

Controller 152 preferably includes a low-power mode of operation and includes an internal clock, such that the controller periodically awakens to communicate with the implantable device to log data or to perform charging functions. Controller 152 preferably is configured to awaken when placed in proximity to the implantable device to perform communications and charging functions, and to transmit commands input using input device 164. Controller 152 further may include programming for evaluating information received from the implantable device, and generating an alarm message on display 159. Controller 152 also may include firmware for transmitting commands input using input device 164 to the implantable device, and monitoring operation of the implantable device during execution of such commands, for example, during boost or jogging/shaking operation of the gear pump to clear a blockage. In addition, controller 152 controls and monitors various power operations of handpiece 151, including operation of inductive circuit 156 during recharging of the implantable device, displaying the state of charge of battery 74, and controlling charging and display of state of charge information for battery 157.

Nonvolatile memory 153 preferably comprises flash memory or EEPROM, and stores the unique device identifier for its associated implantable device, firmware to be executed by controller 152, configuration set point, and optionally, coding to be executed on transceiver 155 and/or inductive circuit 156. Firmware and set point data stored on nonvolatile memory 153 may be updated using information supplied by control and monitoring system 40 via port 162. Volatile memory 154 is coupled to and supports operation of controller 152, and stores data and event log information uploaded from implantable device 20.

In addition, in a preferred embodiment, nonvolatile memory 153 stores programming that enables the charging and communication system to perform some initial start-up functions without communicating with the monitor and control system. In particular, memory 153 may include routines that make it possible to test the implantable device during implantation using the charging and communication system alone in a "self-prime mode" of operation. In this case, a button may be provided that allows the physician to manually start the pump, and display 159 is used to provide feedback whether the pumping session was successful or not. Display 159 of the charging and communication system also may be used to display error messages designed to assist the physician in adjusting the position of the implantable device or peritoneal or bladder catheters. These functions preferably are disabled after the initial implantation of the implantable device.

Transceiver 155 preferably comprises a radio frequency transceiver, e.g., conforming to the Bluetooth or IEEE 802.11 wireless standards, and is configured for bi-directional communications via antenna 160 with transceiver circuit 76 disposed in the implantable device. Transceiver 155 also may include a low power mode of operation, such that it periodically awakens to listen for incoming messages and responds only to those messages including the unique device identifier assigned to its associated implantable device. Transceiver 155 preferably employs an encryption routine to ensure that messages sent to, or received from, the implantable device cannot be intercepted or forged.

Inductive circuit 156 is coupled to coil 163, and is configured to inductively couple with coil 84 of the implantable device to recharge battery 74 of the implantable device. In one embodiment, inductive circuit 156 is coupled to indicator 158, preferably a plurality of LEDs that light to indicate the extent of magnetic coupling between coils 163 and 84 (and thus quality of charging), thereby assisting in positioning handpiece 151 relative to the implantable device. In one preferred embodiment, inductive coils 84 and 163 are capable of establishing good coupling through a gap of 35 mm, when operating at a frequency of 315 kHz or less. In an embodiment in which implantable device includes optional infrared LED 83, charging and communication system 30 may include an optional infrared sensor (not shown) which detects that infrared light emitted by LED 83 and further assists in positioning handpiece 151 to optimize magnetic coupling between coils 163 and 84, thereby improving the energy transmission to the implantable device.

Controller 152 also may be configured to periodically communicate with the implantable device to retrieve temperature data generated by temperature sensor 78 and stored in memory 72 during inductive charging of battery 74. Controller 152 may include firmware to analyze the battery temperature, and to adjust the charging power supplied to inductive circuit 163 to maintain the temperature of the implantable device below a predetermined threshold, e.g., less than 2 degrees C. above body temperature. That threshold may be set to reduce thermal expansion of the battery and surrounding electronic and mechanical components, for example, to reduce thermal expansion of motor and gear pump components and to reduce the thermal strain applied to the seal between lower portion 92 of housing and upper housing 93. In a preferred embodiment, power supplied to inductive coil 163 is cycled between high power (e.g., 120 mA) and low power (e.g., 40 mA) charging intervals responsive to the measured temperature within the implantable device.

As discussed above with respect to inductive circuit 75 of the implantable device, inductive circuit 156 optionally may be configured to transfer additional power to motor 73 of the implantable device, via inductive circuit 75 and battery 74, in a "boost" mode or jogging mode to unblock the gear pump. In particular, if an alarm is transmitted to controller 152 that motor 73 is stalled, e.g., due to a block created by viscous fluid, the patient may be given the option of using input device 164 to apply an overvoltage to motor 73 from inductive circuit 75 for a predetermined time period to free the blockage. Alternatively, activating input device 164 may cause controller 152 to command processor 70 to execute a routine to jog or shake the gear pump by rapidly operating motor 74 in reverse and forward directions to disrupt the blockage. Because such modes of operation may employ higher energy consumption than expected during normal operation, inductive circuits 156 and 75 may be configured to supply the additional energy for such motor operation directly from the energy stored in battery 157, instead of depleting battery 74 of the implantable device.

Battery 157 preferably comprises a lithium ion or lithium polymer battery capable of long lasting operation, e.g., up to three years. Battery 157 has sufficient capacity to supply power to handpiece 151 to operate controller 152, transceiver 155, inductive circuit 156 and the associated electronics while disconnected from base 31 and during charging of the implantable device. In a preferred embodiment, battery 157 has sufficient capacity to fully recharge battery 74 of the implantable device from a depleted state in a period of about 2-4 hours. Battery 157 also should be capable of recharging within about 2-4 hours. It is expected that for daily operation moving 700 ml of fluid, battery 157 and inductive circuit 156 should be able to transfer sufficient charge to battery 74 via inductive circuit 75 to recharge the battery within about 30 minutes. Battery capacity preferably is supervised by controller 152 using a charge accumulator algorithm.

Referring again to FIGS. 7A and 7B, handpiece 151 preferably includes housing 165 having multi-function button 166 (corresponding to input device 164 of FIG. 8) and display 167 (corresponding to display 159 of FIG. 8). A plurality of LEDs 168 is disposed beneath a translucent portion of handpiece 151, and corresponds to indicator 158 of FIG. 8. Port 169 enables the handpiece to be coupled to monitoring and control system 40 (and corresponds to port 162 of FIG. 8), while connector 170 (corresponding to connector 161 in FIG. 8) permits the handpiece to be coupled to base 31 to recharge battery 157. Multi-function button 166 provides the patient the ability to input a limited number of commands to the implantable device. Display 167, preferably an OLED or LCD display, provides visible confirmation that a desired command input using multifunction button 166 has been received. Display 167 also may display the status and state of charge of battery 74 of the implantable device, the status and state of charge of battery 157 of handpiece 151, signal strength of wireless communications, quality-of-charging, error and maintenance messages. Inductive coil portion 171 of housing 165 houses inductive coil 163.

LEDs 168 are visible through the material of housing 165 when lit, and preferably are arranged in three rows of two LEDs each. During charging, the LEDs light up to display the degree of magnetic coupling between inductive coils 163 and 84, e.g., as determined by energy loss from inductive circuit 156, and may be used by the patient to accurately position handpiece 151 relative to the implantable device. Thus, for example, a low degree of coupling may correspond to lighting of only two LEDs, an intermediate degree of coupling with lighting of four LEDs, and a preferred degree of coupling being reflected by lighting of all six LEDs. Using this information, the patient may adjust the position of handpiece 151 over the area where implantable device is located to obtain a preferred position for the handpiece, resulting in the shortest recharging time. In one preferred embodiment, LEDs 168 are replaced with an analog bar display on display 167, which indicates the quality of charge coupling.

The Monitoring and Control System

Figure 9:
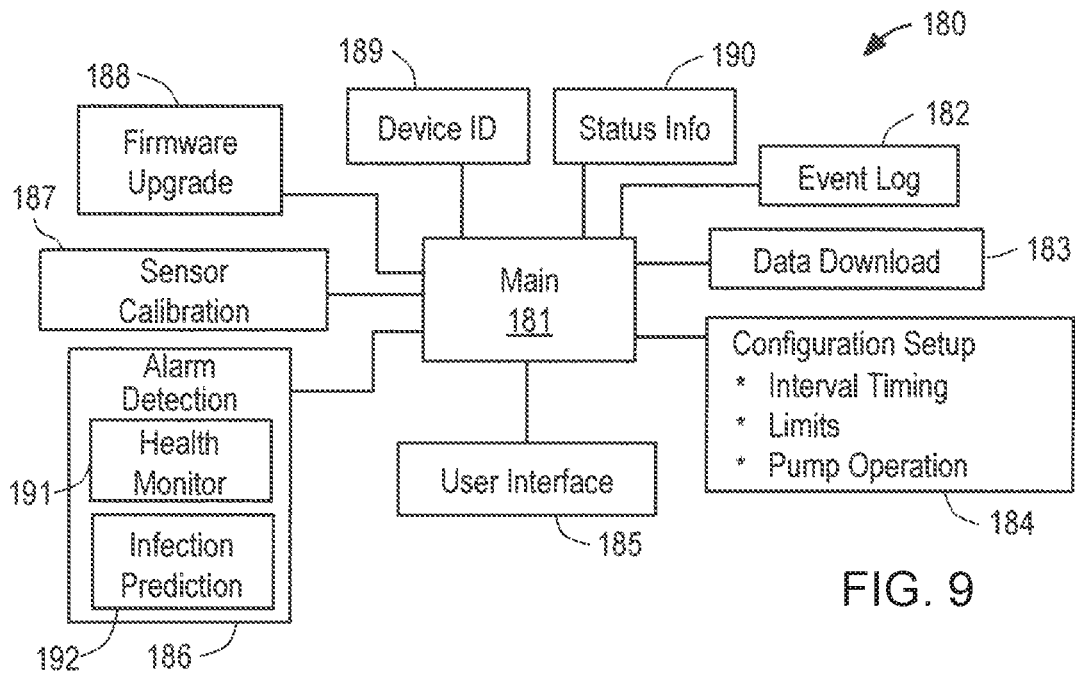
FIG. 9 is a schematic diagram of the software implementing the monitoring and control system for use in practicing the methods of the present invention.

Turning to FIG. 9, the software implementing monitoring and control system of FIG. 1A will now be described. Software 180 comprises a number of functional blocks, schematically depicted in FIG. 9, including main block 184, event logging block 182, data download block 183, configuration setup block 184, user interface block 185, alarm detection block 186 including health monitor block 191 and infection prediction block 192, sensor calibration block 187, firmware upgrade block 188, device identifier block 189 and status information block 190. In one embodiment, the software is coded in C++ and employs an object oriented format, although other software languages and environments could be used. In one embodiment, the software is configured to run on top of a Microsoft Windows® (a registered trademark of Microsoft Corporation, Redmond, Wash.) or Unix-based operating system, such as are conventionally employed on desktop and laptop computers, although other operating systems could be employed.

The computer running monitoring and control system software 180 preferably includes a data port, e.g., USB port or comparable wireless connection that permits handpiece 151 of the charging and communication system to be coupled via port 169. Alternatively, as discussed above, the computer may include a wireless card, e.g., conforming to the IEEE 802.11 standard, thereby enabling handpiece 151 to communicate wirelessly with the computer running software 180. As a further alternative, the charging and communication system may include telephony circuitry that automatically dials and uploads data, such as alarm data, from handpiece 151 to a secure website accessible by the patient's physician.

Main block 184 preferably consists of a main software routine that executes on the physician's computer, tablet or smartphone, and controls overall operation of the other functional blocks. Main block 184 enables the physician to download event data and alarm information stored on handpiece 151 to their computer, tablet or smartphone, and also permits control and monitoring software 180 to directly control operation of the implantable device when coupled to handpiece 151. Main block also enables the physician to upload firmware updates and configuration data to the implantable device.

Event Log block 182 is a record of operational data downloaded from the implantable device via the charging and communication system, and may include, for example, pump start and stop times, motor position, sensor data for the peritoneal cavity and bladder pressures, patient temperature, respiratory rate or fluid temperature, pump outlet pressure, humidity, pump temperature, battery current, battery voltage, battery status, and the like. The event log also may include the occurrence of events, such as pump blockage, operation in boost or jog modes, alarms or other abnormal conditions.

Data Download block 183 is a routine that handles communication with handpiece 151 to download data from volatile memory 154 after the handpiece is coupled to the computer running monitoring and control software 180. Data Download block 183 may initiates, either automatically or at the instigation of the physician via user interface block 185, downloading of data stored in the event log.

Configuration Setup block 184 is a routine that configures the parameters stored within nonvolatile memory 71 that control operation of the implantable device. The interval timing parameters may determine, e.g., how long the processor remains in sleep mode prior to being awakened to listen for radio communications or to control pump operation. The interval timing parameters may control, for example, the duration of pump operation to move fluid from the peritoneal cavity to the bladder and the interval between periodic tick movements that inhibit blockage of the implantable device and peritoneal and bladder catheters. Interval timing settings transmitted to the implantable device from monitoring and control software 180 also may determine when and how often event data is written to nonvolatile memory 71, and to configure timing parameters used by the firmware executed by processor 152 of handpiece 151 of the charging and communication system. Block 184 also may be used by the physician to configure parameters stored within nonvolatile memory 71 relating to limit values on operation of processor 70 and motor 73. These values may include minimum and maximum pressures at the peritoneal and bladder catheters, the maximum temperature differential during charging, times when the pump may and may not operate, etc. The limit values set by block 184 also configure parameters that control operation of processor 152 of handpiece 151.

Block 184 also may configure parameters store within nonvolatile memory 71 of the implantable device relating to control of operation of processor 70 and motor 73. These values may include target daily volumes of fluid to transport, volume of fluid to be transported per pumping session, motor speed and duration per pumping session. Block 184 also may specify the parameters of operation of motor 73 during boost mode of operation, when coupled to handpiece 151, and shake/jog modes of operation when the implantable device is run using battery 74 alone. Such parameters may include motor speed and voltage, duration/number of revolutions of the motor shaft when alternating between forward and reverse directions, etc.

User interface block 185 handles display of information retrieved from the monitoring and control system and implantable device via data download block 183, and presents that information in an intuitive, easily understood format for physician review. As described below with respect to FIGS. 10 to 14, such information may include status of the implantable device, status of the charging and control system, measured pressures, volume of fluid transported per pumping session or per day, etc. User interface block 185 also generates user interface screens that permit the physician to input information to configure the interval timing, limit and pump operation parameters discussed above with respect to block 184.

Alarm detection block 186 may include a routine for evaluating the data retrieved from the implantable device or charging and communication system, and flagging abnormal conditions for the physician's attention. For example, alarm detection block 186 may include health monitor block 191, which is configured to alert the physician to any changes in the patient's health that may warrant changing the volume, time, and/or frequency with which the DSR infusate is provided to the patient's peritoneal cavity. For example, if data provided by the implantable device 20 indicate a buildup of fluid in the peritoneal cavity, then the physician may increase the volume, time, and/or frequency with which the fluid is withdrawn from the patient's peritoneal cavity. Or, if data provided by the implantable device 20 indicate a relatively low volume of fluid, then the physician may decrease the volume, time, and/or frequency with which the fluid is withdrawn from the patient's peritoneal cavity.

Alarm detection block 186 also, or alternatively, may include decompensation prediction block 192, which is configured to predict or detect heart failure decompensation based on, for example, one or more of an increase in the accumulation of fluid in the patient's peritoneal cavity above a predefined threshold, an increase in the patient's respiratory rate above a predefined threshold, and/or an increase in the intraabdominal pressure above a predefined threshold. Such flags may be communicated to the physician by changing status indicators presented by user interface block 185, or by displaying to the physician specific information about increases in the patient's fluid accumulation, respiratory rate, or intraabdominal pressure via user interface block 185.

Sensor calibration block 187 may include a routines for testing or measuring drift, of sensors 70, 78-81 employed in the implantable device, e.g., due to aging or change in humidity. Block 187 may then compute offset values for correcting measured data from the sensors, and transmit that information to the implantable device for storage in nonvolatile memory 71. For example, pressure sensors 104a-104d may experience drift due to aging or temperature changes. Block 187 accordingly may compute offset values that are then transmitted and stored in the implantable device to account for such drift.

Firmware upgrade block 188 may comprise a routine for checking the version numbers of the processor or motor controller firmware installed on the implantable device and/or processor firmware on charging and communication system, and identify whether upgraded firmware exists. If so, the routine may notify the physician and permit the physician to download revised firmware to the implantable device for storage in nonvolatile memory 71 or to download revised firmware to the charging and communication system for storage in nonvolatile memory 153.

Device identifier block 189 consists of a unique identifier for the implantable device that is stored in nonvolatile memory 71 and a routine for reading that data when the monitoring and control system is coupled to the implantable device via the charging and communication system. As described above, the device identifier is used by the implantable device to confirm that wireless communications received from a charging and communication system are intended for that specific implantable device. Likewise, this information is employed by handpiece 151 of the charging and communication system in determining whether a received message was generated by the implantable device associated with that handpiece. Finally, the device identifier information is employed by monitoring and control software 180 to confirm that the handpiece and implantable device constitute a matched set.

Status information block 190 comprises a routine for interrogating implantable device, when connected via handpiece 151, to retrieve current status date from the implantable device, and/or handpiece 151. Such information may include, for example, battery status, the date and time on the internal clocks of the implantable device and handpiece, version control information for the firmware and hardware currently in use, and sensor data.

Figure 10:
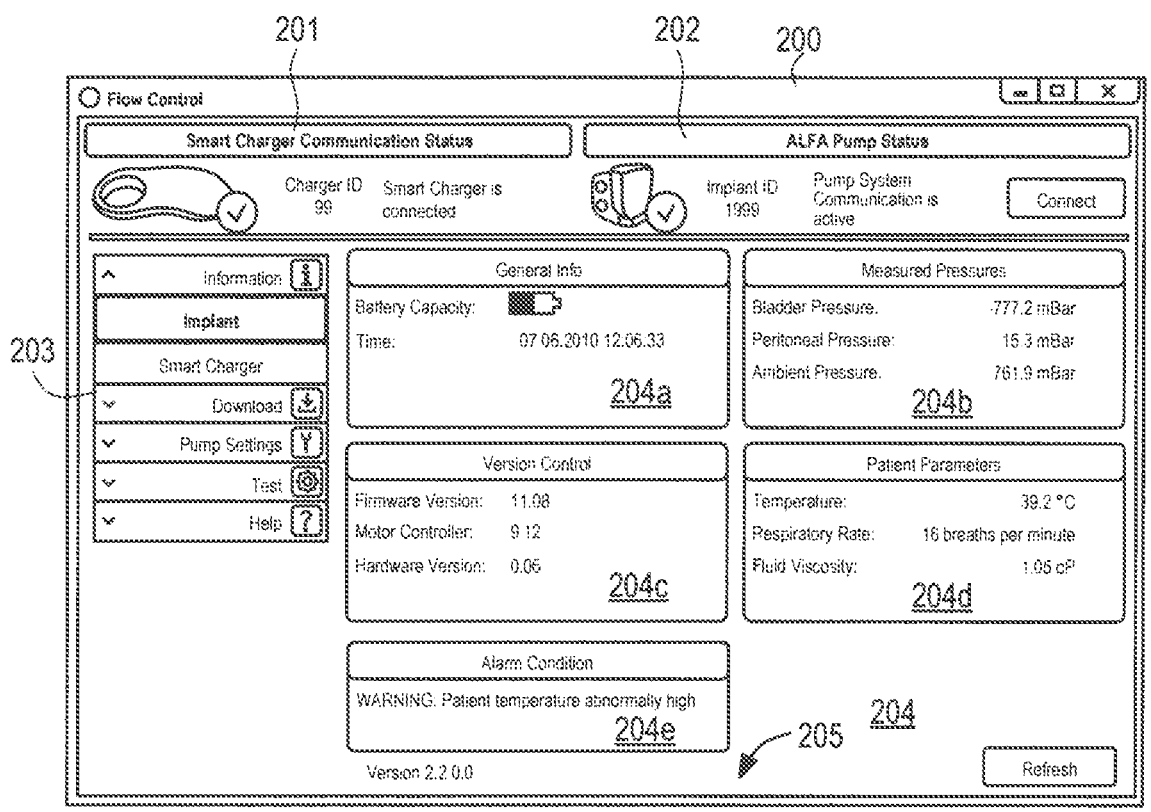
FIG. 10 is a screen display of the main screen that is displayed to a physician running monitoring and control software.

Referring now to FIGS. 10-14, exemplary screen shots generated by user interface block 187 of software 180 are described for an implantable system used in accordance with the methods of the present invention to treat HF. FIG. 10 shows main screen 200 that is displayed to a physician running monitoring and control software 180. Main screen 200 includes a status area that displays status information retrieved from the implantable device and the charging and communication system by the routine corresponding to block 190 of FIG. 9. More particularly, the status area includes status area 201 for the charging and communication system (referred to as the "Smart Charger") and status area 202 for the implantable device (referred to as the "ALFA Pump"). Each status area includes an icon showing whether the respective system is operating properly, indicated by a checkmark, the device identifier for that system, and whether the system is connected or active. If a parameter is evaluated by the alarm detection block 186 to be out of specification, the icon may instead include a warning symbol. Menu bar 203 identifies the various screens that the physician can move between by highlighting the respective menu item. Workspace area 204 is provided below the status area, and includes a display that changes depending upon the menu item selected. Below workspace area 204, navigation panel 205 is displayed, which includes the version number of software 180 and a radio button that enables the displays in workspace area 204 to be refreshed.

In FIG. 10, the menu item "Information" with submenu item "Implant" is highlighted in menu bar 203. For this menu item selection, workspace area 204 illustratively shows, for the implantable device, battery status window 204a, measured pressures window 204b and firmware version control window 204c. Battery status window 204a includes an icon representing the charge remaining in battery 74, and may be depicted as full, three-quarters, one-half, one-quarter full or show an alarm that the battery is nearly depleted. The time component of window 204a indicates the current time as received from the implantable device, where the date is expressed in DD/MM/YYYY format and time is expressed in HR/MIN/SEC format based on a 24 hour clock. Measured pressures window 204b displays the bladder pressure, peritoneal pressure and ambient pressures in mBar measured by sensors 104a, 104b and 104d respectively (see FIG. 6A). Version control window 204c indicates the firmware version for processor 70, for the motor controller, and the hardware version of the implantable device. Patient parameters window 204d displays the patient's temperature, respiratory rate, and intraabdominal pressure. Note that if implantable device included other types of sensors, e.g., sensors that measure the levels of fluid in the body, then the parameters measured by such sensors could also be displayed in window 204d.

Alarm condition window 204e displays any changes in parameters that may indicate a change in the patient's health, such as the possible development of heart failure decompensation or an improvement or worsening of the patient's health (Blocks 191 and 192 in FIG. 9). For example, as illustrated, alarm condition window 204e may alert the physician that the patient's intra-abdominal pressure is abnormally high, so that the physician then may follow up with the patient regarding the possibility of decompensation. In some embodiments, based on information displayed in windows 204b, 204d, and/or 204e, the physician may adjust the operating parameters of the pump, e.g., using the interface described further below with reference to FIG. 13.

Figure 11:
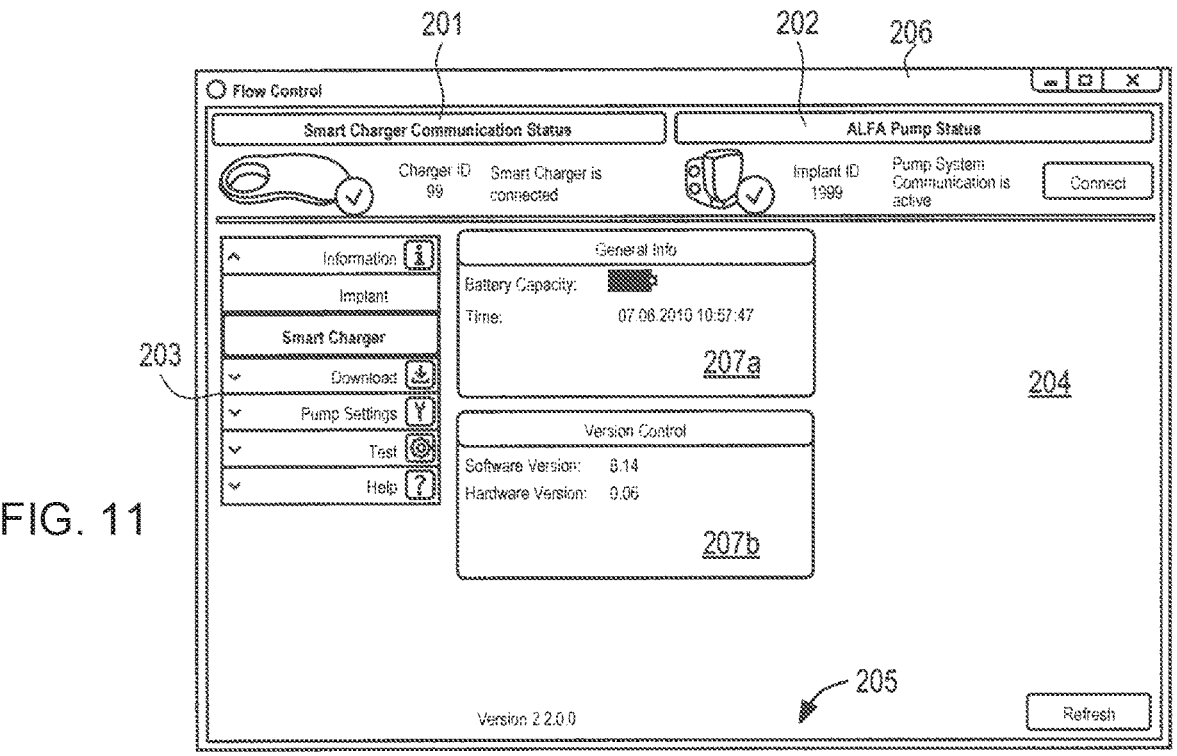
FIG. 11 is a screen display of the selection of the "Smart Charger" submenu item in FIG. 10.

Turning to FIG. 11, screen display 206 corresponding to selection of the "Smart Charger" submenu item in FIG. 10 is described. FIG. 11 includes status area 201 for the charging and communication system, status area 202 for the implantable device, menu bar 203, workspace area 204, and navigation panel 205 as discussed above with respect to FIG. 10. Screen display 206 differs from screen display 200 in that the "Smart Charger" submenu item is highlighted, and workspace area 204 displays, for the charging and control system, battery status window 207a and version control window 207b. Battery status window 207a includes an icon representing the charge remaining in battery 157, and may be depicted as full, three-quarters, one-half, one-quarter full or show an alarm that the battery is nearly depleted. The time component of window 207a indicates the current time as received from handpiece 151, where the date is expressed in DD/MM/YYYY format and time is expressed in HR/MIN/SEC format based on a 24 hour clock. Version control window 207b indicates the firmware version for processor 152, and the hardware version of the charging and control system.

Figure 12:
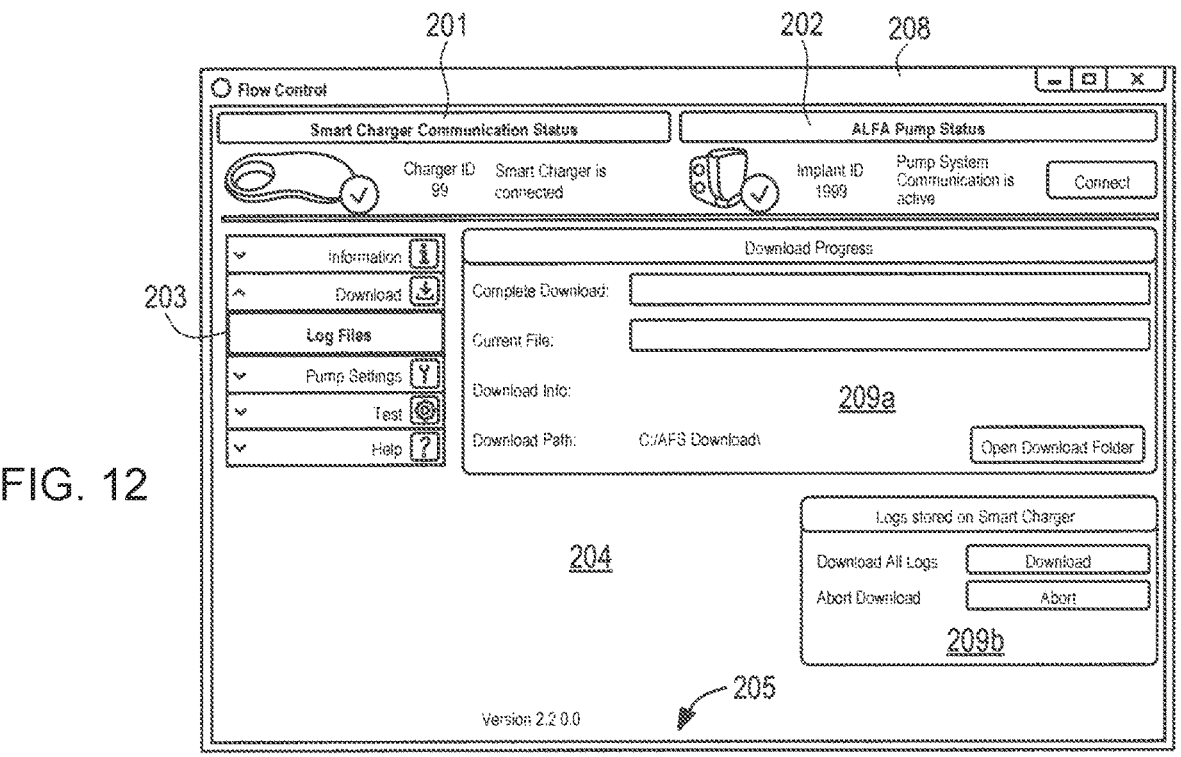
FIG. 12 is a screen display of the selection of the "Download" menu item in FIG. 10 and "Log Files" submenu item.

Referring now to FIG. 12, screen display 208 corresponding to selection of the "Download" menu item in FIG. 10 and "Log Files" submenu item is described, and implements the functionality of block 183 of software 180. FIG. 12 includes status area 201 for the charging and communication system, status area 202 for the implantable device, menu bar 203, workspace area 204, and navigation panel 205, all as discussed above. Screen display 208 differs from the "Information" screen display in that the "Log Files" submenu item is highlighted, and workspace area 204 displays download progress window 209a and storage path window 209b. Window 209a includes the path for the directory to which event logs may be downloaded from the implantable device via the charging and communication system. Window 209a also includes an "Open Download Folder" radio button that allows the physician to choose the directory path to which the event logs are downloaded, and a progress bar that is updated to reflect the amount of data downloaded. Window 209b includes a radio button that can be activated to download the event log to the path specified in window 209a, and also includes an "Abort" radio button to interrupt the download process.

Figure 13:
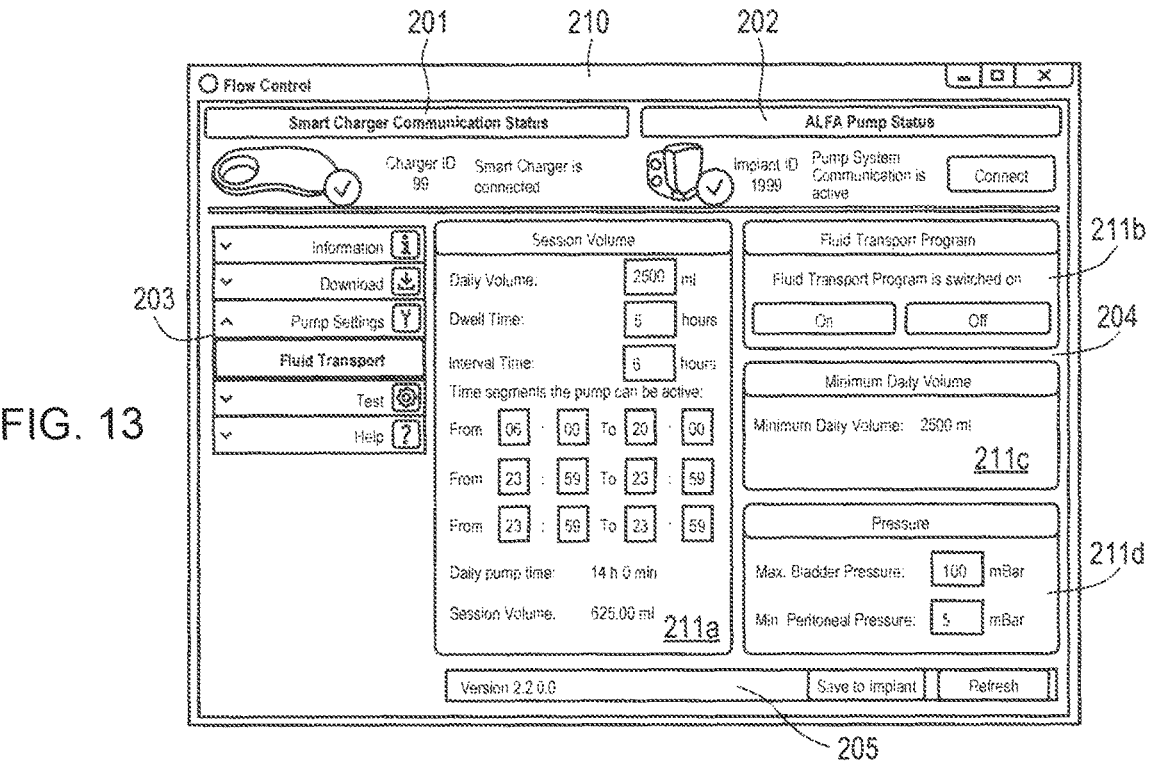
FIG. 13 is a screen display of the selection of the "Pump Settings" menu item in FIG. 10 and "Fluid Transport" submenu item.

FIG. 13 is an exemplary depiction of screen display 210, corresponding to selection of the "Pump Settings" menu item in FIG. 10 and "Fluid Transport" submenu item, and implements the functionality of blocks 184 and 190 of software 180. FIG. 13 includes status area 201 for the charging and communication system, status area 202 for the implantable device, menu bar 203, workspace area 204, and navigation panel 205, all as discussed above. Screen display 210 differs from the "Information" screen displays in that the "Fluid Transport" submenu item is highlighted, and workspace area 204 includes session volume window 211a, fluid transport program window 211b, minimum daily volume window 211c, pressure window 211d, and a radio button in navigation panel 205 that permits values entered in windows 211a, 211b and 211d to be transmitted and stored in non-volatile memory 71 of the implantable device.

Session volume window 211a displays the current setting for the interval time between pumping sessions of the fluid that naturally accumulates in the peritoneal cavity, the times of the day that the pump may be activated, the total daily pump time and the session volume per pumping session. The dwell time displayed in window 211a allows the physician to set the amount of time that the DSR infusate is to remain in the peritoneal cavity. The interval time displayed in window 211a allows the physician to set the frequency with which the sodium-laden DSR infusate and osmotic ultrafiltrate are extracted from the peritoneal cavity and directed to the bladder (as well as the DSR infusate from the reservoir to the peritoneal cavity). The volume of DSR infusate delivered from the reservoir, dwell times and extraction times are used by the configuration setup routine (block 184 of FIG. 9) to determine overall operation of the system.

The time segments that the pump may be active, displayed in window 211a, optionally may be used define the timeframes during which the implantable device can actively move fluid to the bladder; outside of these time segments, the implantable device will not move fluid but may implement the pump tick operation described above to turn the gears on a regular basis to prevent clogging of the gears. Depending on the perceived health of the patient, the physician may set the time segments such that the pump may operate at all hours of the day or night, as preservation of health may override convenience in some circumstances. The daily pump time displayed in window 211a is shown in read-only format because it is the aggregate of the time segments entered in the time segments boxes. Finally, the session volume displayed in window 211a is computed by block 183 as the amount of fluid transferred to the bladder in a single pumping session.

Fluid transport program window 211b displays the status of the program controlling operation of the pump of the implantable device based on the parameters set using block 184 of software 180. In case pump activity must be stopped for any reason, the fluid transport program can be stopped by clicking the "Off" button in window 211b, which will cause the pump to stop pumping until it is manually switched back on. In one embodiment, the fluid transport program may switched on again by pressing the "On" button in window 211b. Because the implantable device preferably is implanted with the pump turned off, the physician or surgeon may use window 211b to turn on the fluid transport program after the implantable device is first implanted.

Minimum daily volume window 211c displays the expected amount of fluid to be pumped to the bladder by the implantable device, and is computed by the configuration setup routine as the session volume times the number of sessions per day, based on the length of the prescribed time segments and interval timing input in window 211a.

Pressure window 211d of FIG. 13 permits the physician to input values of maximum bladder pressure and minimum peritoneal pressure that are used to control operation of the implantable pump. Thus, for example, processor 70 will command motor 73 to cease a current pumping session, or to skip a planned pumping session during the time segments identified in window 211a, if the bladder pressure detected by the pressure sensors exceeds the value specified in window 211d. Likewise, processor 70 will command motor 73 to cease a current pumping session, or to skip a planned pumping session during the time segments identified in window 211a, if the peritoneal pressure detected by the pressure sensors is less than the value specified in window 211d. If configured to operate in the above-described manner, the implantable device will neither cause patient discomfort by overfilling the patient's bladder, nor cause the peritoneal cavity to become excessively dry.

Figure 14:
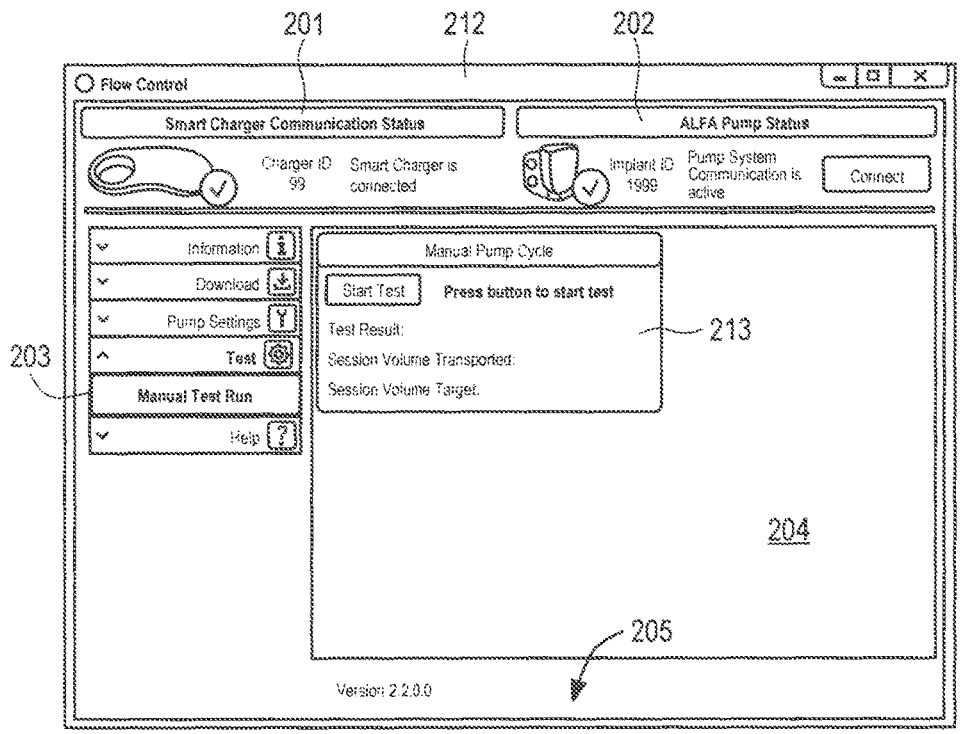
FIG. 14 is a screen display of the selection of the "Test" menu item in FIG. 11 and "Manual Test Run" submenu item.

Referring now to FIG. 14, an exemplary depiction of screen display 212, corresponding to selection of the "Test" menu item in FIG. 11 and "Manual Test Run" submenu item is described. FIG. 14 includes status area 201 for the charging and communication system, status area 202 for the implantable device, menu bar 203, workspace area 204, and navigation panel 205, all as discussed above. Screen display 212 differs from the "Information" screen displays in that the "Manual Test Run" submenu item is highlighted, and workspace area 204 includes manual pump cycle window 213. Manual pump cycle window 213 includes radio button "Start Test" which transmits a command to the implantable device via the charging and communication system to cause processor 70 to activate the pump for a predetermined period of time, e.g., a few seconds. Processor 70 receives positional data from the Hall Effect sensors in motor 73 and measured pressure data across pressure sensors 104c and 104d. Processor 70 computes a session volume and relays that information via the charging and communication system back to software 10, which compares the measured data to a target session volume and provides a test result, e.g., percentage of session target volume achieved or pass/fail icon. The measured session volume, session target volume and test result are displayed in window 213.

While various illustrative embodiments of the invention are described above, it will be apparent to one skilled in the art that various changes and modifications may be made therein without departing from the invention. For example, system 10 may be modified to include additional devices configured to assess the physical and/or mental health of the patient, such as weighing scales, ECG or heart-rate sensors or a hand-held biosensor that measures the levels of sodium and/or toxins and/or waste products, e.g., ammonia, c-reactive protein, plasma renin, serum sodium, serum creatinine, prothrombin time, and/or bilirubin, in a drop of the patient's blood. If coupled to sensor that measures serum creatinine, the system may be configured to calculate and store a current value of GFR using the equation set forth above. If so configured, the system could issue an alert to the physician to discontinue the use of no or low sodium DSR infusate if the GFR is computed to fall below 15.

Alternatively, or in addition, system 10 may be modified to include a hand-held or computer-based device that presents the patient with psychometric tests that measure the psychological health or electrophysiological activity of the subject. Such devices may be configured to wirelessly provide results to monitoring and control system 40 for the physician to use in assessing the patient's health and the possible need to adjust the operating parameters of implantable device 20. The appended claims are intended to cover all such changes and modifications that fall within the true spirit and scope of the invention.

Preliminary Experimental Results

Initial testing of the DSR infusate and methods of the present invention has been conducted in a porcine model, which is expected to provide valid insights into how the inventive system, methods and DSR infusate will behave in humans. That initial testing has provided remarkably successful and beneficial results that far exceeded expectations, as described in further detail below.

In a first group of five pigs ("protocol refinement pigs"), the effect of infusing 1 liter of sodium-free DSR infusate into the peritoneal cavity of each pig was measured. The DSR infusate generally comprised purified water and dextrose, e.g., 10 grams per 100 ml of water, and was allowed to dwell in their peritoneal cavities for up to six hours. 5-25 micro curies of I-131 radiolabled albumin was mixed into the infusate as a non-absorbable tracer to determine ultrafiltration kinetics without requiring serial drains of the abdomen. Throughout the dwell period, the fluid in the peritoneal cavities was sampled to determine total sodium removed and sodium concentration in the fluid accumulating in the peritoneal cavity as a function of time, and blood samples were taken as well. Specifically, in the 1½ hours after infusion of the DSR infusate, 3 ml blood sample and 2.5 ml fluid samples were taken every 15 minutes and analyzed. In the next 1½ hour period, blood and fluid samples were taken every ½ hour. And in the final 3 hours, additional blood and fluid samples were taken every hour. In addition, the total volume of fluid accumulated in the peritoneal cavity, consisting of sodium-laden DSR infusate and osmotic ultrafiltrate, was recorded as a function of time.

Figure 15A:
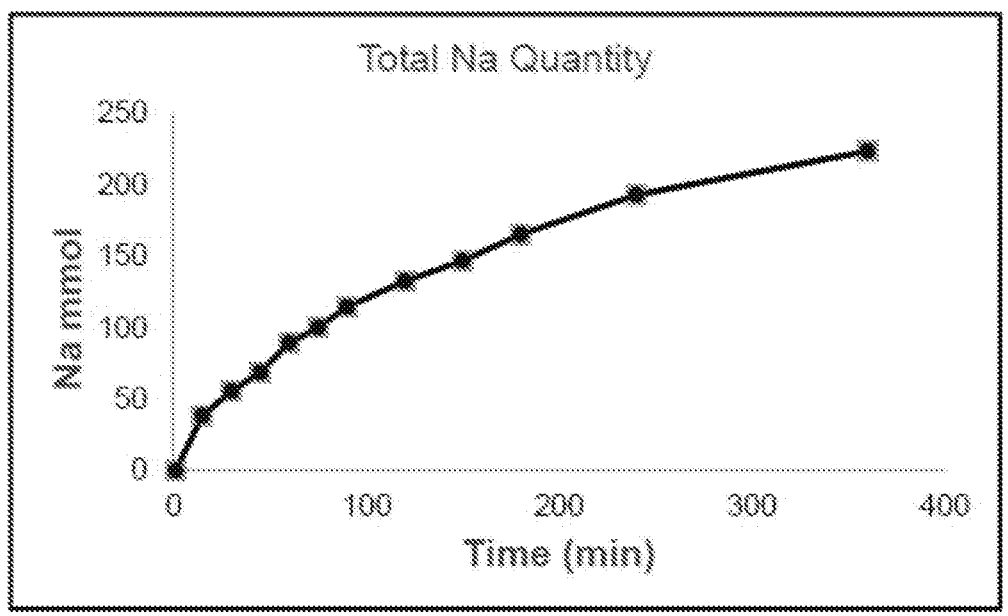
FIGS. 15A, 15B and 15C are graphs depicting the results of testing of the inventive DSR method on an initial group of five animals.
Figure 15B:
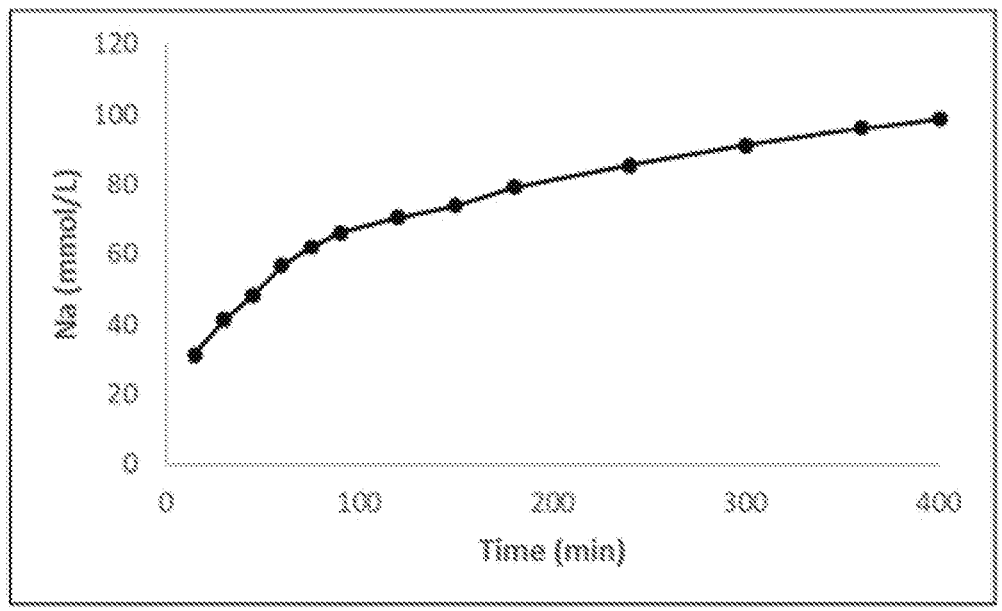
Figure 15C:
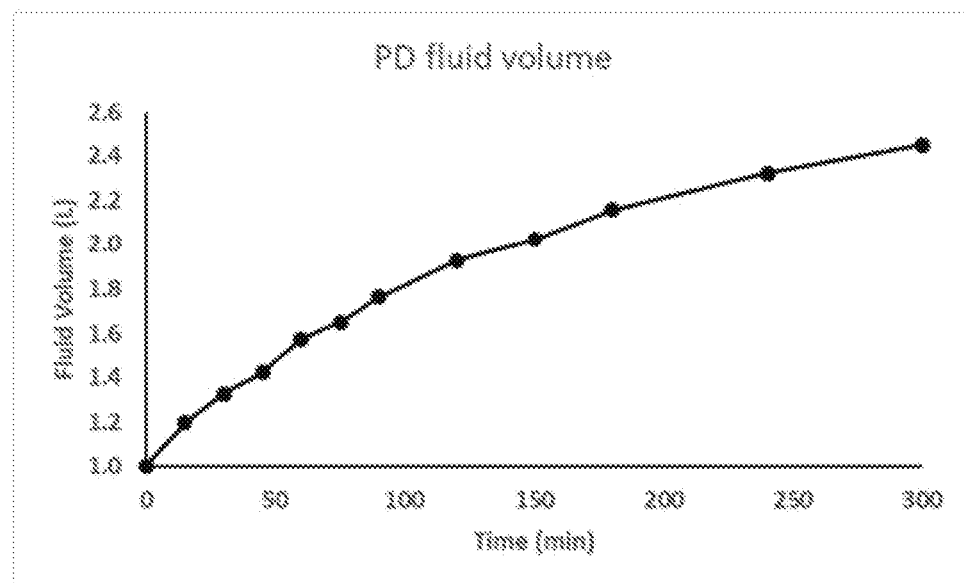

FIG. 15A shows the total amount of sodium removed as a function of dwell time for the first group of pigs, while FIG. 15B shows the sodium concentration in the samples removed from the peritoneal cavities as a function of time. FIG. 15C depicts the total volume of fluid accumulated in the peritoneal cavities of the first group of pigs. As depicted in FIG. 15C, surprisingly, after two hours, infusion of 1 liter of DSR infusate induced 1 liter of osmotic filtrate to accumulate in the peritoneal cavity.

In a second group of ten pigs ("protocol pigs"), 1 liter of DSR infusate was infused in the peritoneal cavities of each pig for a two hour dwell period. Throughout the dwell period serum sodium, serum osmolality, plasma osmolality and glucose levels of the pigs were periodically measured by taking 6 ml blood samples every ½ hour. Total osmolality, glucose osmolality and non-glucose osmolality of the fluid accumulating in the peritoneal cavities were periodically measured during the dwell period using the foregoing samples. After completion of the dwell period, the total volume of fluid drained from the peritoneal cavity and the total amount of sodium removed, was measured.

Figure 16A:
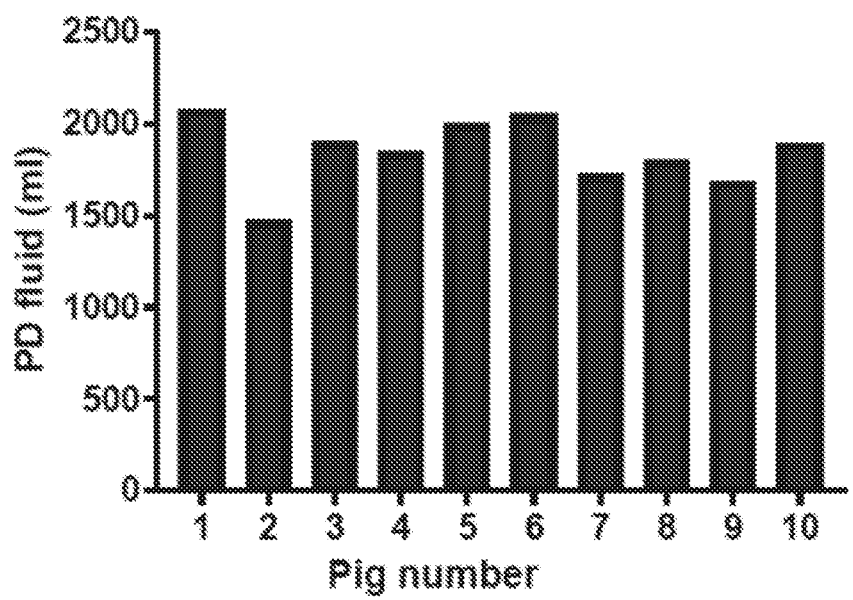
FIGS. 16A to 16F are graphs depicting the results of testing of the inventive DSR method on a follow-up group of ten animals.
Figure 16B:
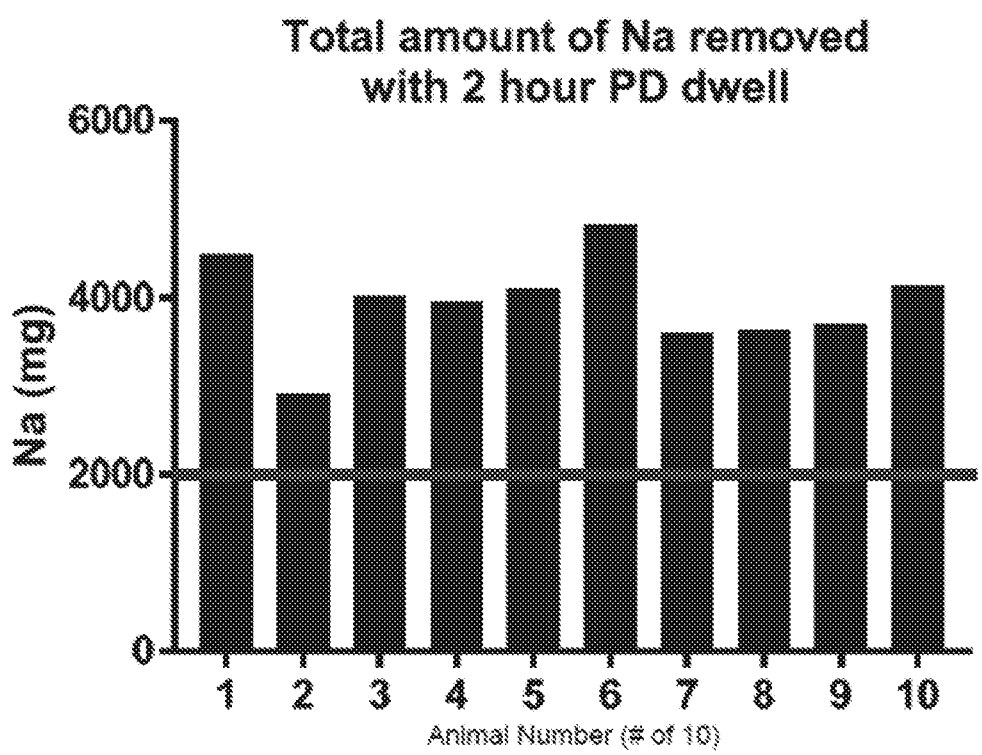
Figure 16C:
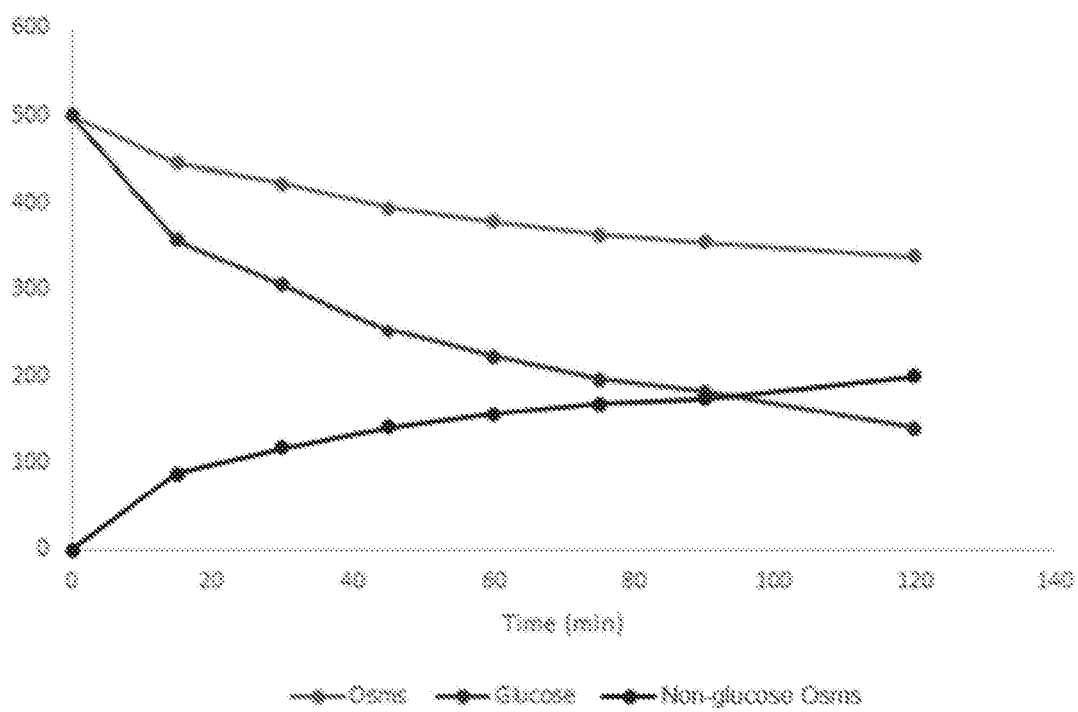
Figure 16D:
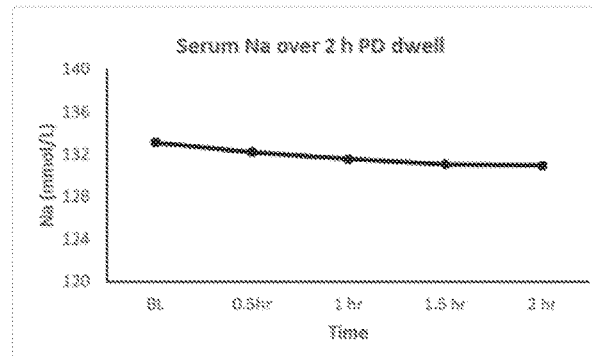
Figure 16E:
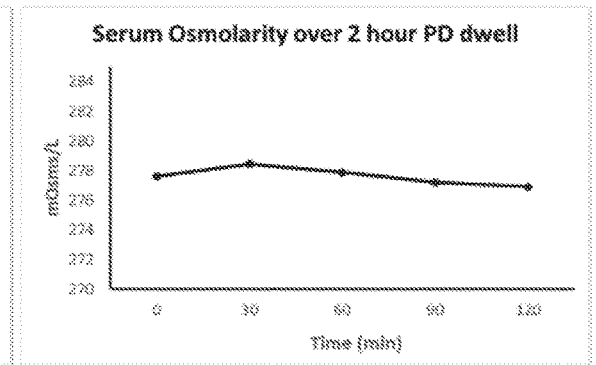
Figure 16F:
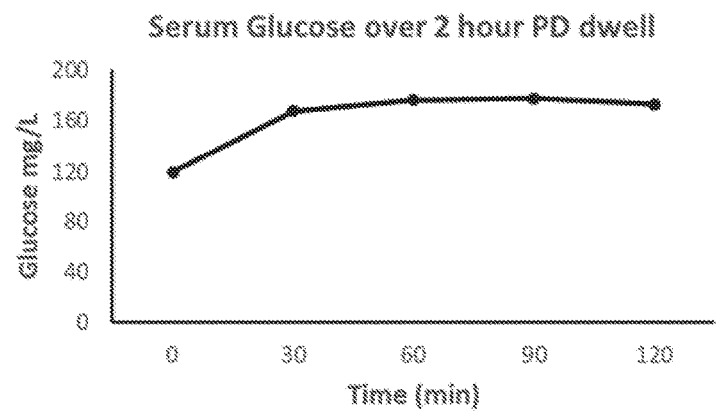

FIG. 16A is a chart showing the total fluid volume removed from the peritoneal cavity of each protocol pig after a two-hour dwell. FIG. 16B shows the total amount of sodium removed from the peritoneal cavity of each protocol pig after a two-hour dwell. FIG. 16C shows the evolution of total osmolality, glucose osmolality, and non-glucose osmolality for samples of fluid from the peritoneal cavities of the protocol pigs throughout the two-hour dwell period. FIGS. 16D, 16E and 16F show the evolution of serum sodium, serum osmolality, and serum glucose, respectively, for the protocol pigs throughout the two-hour dwell period. The foregoing results demonstrate that the inventive DSR methods and infusates remove a clinically relevant amount of sodium, e.g., 4000 mg, with a single administration of 1 liter of DSR infusate and a two hour dwell, but with clinically negligible impact on serum sodium levels. The 4000 mg of sodium removed is generally equivalent to two days of recommended sodium consumption, which will induce the elimination of stored fluid via urination and direct removal of a significant (1 liter with the studied parameters) accumulation of osmotic ultrafiltrate from the peritoneal cavity. And as shown in FIGS. 16D, 16E and 16F, the single administration of DSR infusate with a two hour dwell is expected to be very safe, as serum sodium level and serum osmolality remained stable throughout the period with only an expected and clinically manageable increase of serum glucose concentration.

Figure 17A:
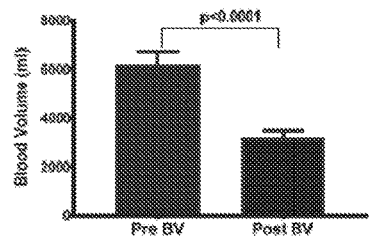
FIGS. 17A to 17C are graphs depicting changes to blood volume, red blood count, and plasma volume for a sub-group of the second group of animals after consecutive applications of the inventive DSR method.
Figure 17B:
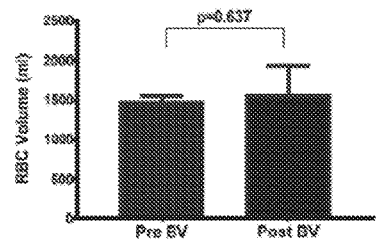
Figure 17C:
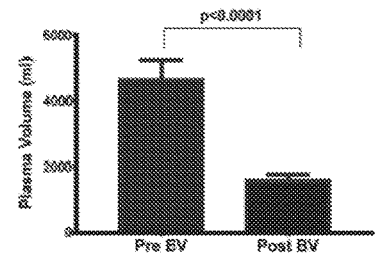

FIGS. 17A-17C depicts the measurements for a number of blood volume markers in a sub-group of five of the protocol pig population both before and after repeated application of the inventive methods. FIG. 17A shows almost a ½ reduction in the total blood volume of the protocol pigs after five cycles of DSR treatment. As expected, FIG. 17B shows virtually no impact of the DSR method on the total volume of red blood cells. However, FIG. 17C shows that there is a reduction in plasma volume of approximately 60%. Accordingly, as depicted in FIGS. 17A-17C, repeated use of the DSR method of the present invention is demonstrated to achieve a significant reduction in blood volume by reducing plasma volume. This demonstrates the effectiveness of the DSR method of the present invention and how it may be used to eliminate different levels of fluid overload.

Figure 18:
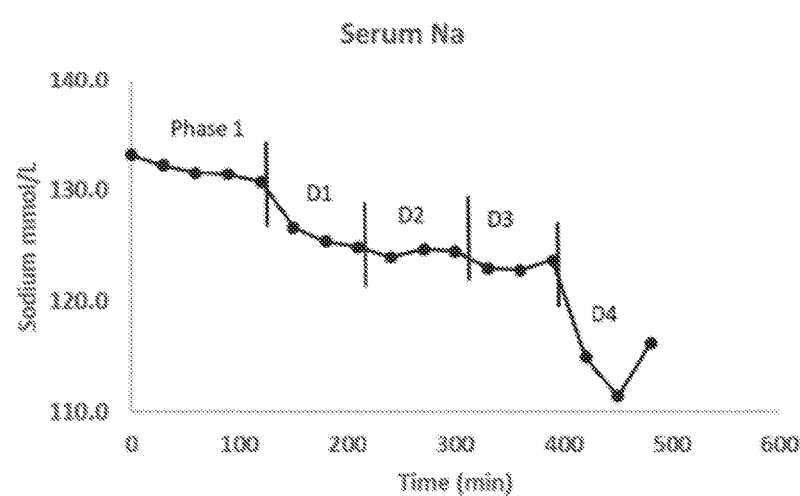
FIG. 18 is a graph depicting the changes to serum sodium level for animals in the sub-group of the second group of animals after consecutive applications of the DSR method.

FIG. 18 shows the impact on serum sodium concentration in the same sub-group of five of the protocol pigs to investigate the impact of use of the inventive DSR infusate in patients with reduced residual renal function was conducted. As shown in FIG. 18, serial application of the method of the present invention without the pigs having an opportunity to restore the loss of sodium and fluid lead to severe reductions in serum sodium levels. The pigs were effectively anephric due to the severe renal injury from blood volume depletion. FIGS. 17A-C and FIG. 18 suggest that use of a no or low sodium infusate in patients with severe renal dysfunction (i.e. CKD of Stage 5 or GFR<15 ml/min/1.73 m$^2$) in volumes adequate for dialysis would lead to dangerous or terminal hyponatremia and reduction in plasma volume leading to hemodynamic collapse. Accordingly, as described above, the DSR method, infusate and apparatus of the present invention should be targeted to those patients experiencing fluid overload and heart failure who still have a GFR value greater than 15 or CKD of Stage 4 or lower.

While various illustrative embodiments of the invention are described above, it will be apparent to one skilled in the art that various changes and modifications may be made therein without departing from the invention. For example, pump system 1 may be ordered differently and may include additional or fewer components of various sizes and composition. The appended claims are intended to cover all such changes and modifications that fall within the true spirit and scope of the invention.

What is claimed is:

1. A method of using a no or low sodium direct sodium removal ("DSR") infusate to treat a patient having heart failure with fluid overload, the patient having an estimated glomerular filtration rate greater than 15 ml/min/1.73 m$^2$, the method comprising:
providing a DSR infusate comprising an aqueous solution containing at least one of 0.5 to 50 grams of dextrose per 100 ml of aqueous solution, 0.5 to 50 grams of icodextrin per 100 ml of aqueous solution, 0.5 to 50 grams of a high molecular weight glucose polymer having an average molecular weight greater than 10,000 Daltons per 100 ml of aqueous solution, or any combination thereof, and having a sodium concentration equal to or less than 35 meq/L;
introducing the DSR infusate into a peritoneal cavity of the patient;
inducing sodium and osmotic ultrafiltrate to accumulate with the DSR infusate in the peritoneal cavity during a dwell period; and
removing the DSR infusate, sodium and osmotic ultrafiltrate from the peritoneal cavity of the patient to alleviate fluid overload and restore serum sodium concentrations, while preventing hyponatremia.

2. The method of claim 1, wherein the removing the DSR infusate, sodium and osmotic ultrafiltrate further comprises eliminating fluid from the patient through urination caused by kidney functioning.

3. The method of claim 1, wherein the DSR infusate further comprises one or more of an electrolyte selected from a magnesium salt and a calcium salt; an antifungal agent, and a buffering agent.

4. The method of claim 1, wherein the introducing the DSR infusate into a peritoneal cavity of the patient comprises transferring the DSR infusate into the peritoneal cavity of the patient from a reservoir using an implantable pump.

5. The method of claim 1, wherein the introducing the DSR infusate into a peritoneal cavity of the patient comprises infusing the DSR infusate into the peritoneal cavity of the patient using gravity to deliver the DSR infusate from a reservoir.

6. The method of claim 1, wherein the introducing the DSR infusate into a peritoneal cavity of the patient comprises delivering the DSR infusate using an extracorporeal pump, pressurized container, or gravity based feeding system.

7. The method of claim 1, wherein the removing the DSR infusate including the sodium and osmotic ultrafiltrate from the peritoneal cavity of the patient comprises, upon expiration of the dwell period, transferring the DSR infusate, sodium and osmotic ultrafiltrate from the peritoneal cavity to a urinary bladder of the patient using an implantable pump.

8. The method of claim 7, further comprising activating the implantable pump at predetermined times to transfer a predetermined volume of the DSR infusate, sodium and osmotic ultrafiltrate from the peritoneal cavity to the urinary bladder of the patient.

9. The method of claim 1, further comprising, during the dwell period, monitoring the intra-abdominal pressure of the patient with one or more sensors.

10. The method of claim 9, further comprising, during the dwell period, monitoring the rate of fluid accumulation in the peritoneal cavity.

11. The method of claim 10, further comprising, during the dwell period, generating an alert to a physician indicative of the increase in the rate of fluid accumulation in the peritoneal cavity or increase in intra-abdominal pressure.

12. A method of treating a patient having heart failure with fluid overload, the patient having kidney function from normal to CKD Stage 4, the method comprising:
providing a direct sodium removal ("DSR") infusate comprising an aqueous solution containing at least one of 0.5 to 50 grams of dextrose per 100 ml of aqueous solution, 0.5 to 50 grams of icodextrin per 100 ml of aqueous solution, 0.5 to 50 grams of a high molecular weight glucose polymer having an average molecular weight greater than 10,000 Daltons per 100 ml of aqueous solution, or any combination thereof, the aqueous solution being essentially sodium-free;
introducing the DSR infusate into a peritoneal cavity of the patient;
inducing sodium and osmotic ultrafiltrate to accumulate with the DSR infusate in the peritoneal cavity during a dwell period;
removing the DSR infusate, sodium and osmotic ultrafiltrate from the peritoneal cavity to alleviate the fluid overload; and
removing fluid from the patient by urination to restore serum sodium concentrations, while preventing hyponatremia.

13. The method of claim 12, wherein the DSR infusate further comprises one or more of an electrolyte selected from a magnesium salt and a calcium salt; an antifungal agent, and a buffering agent.

14. The method of claim 12, wherein the introducing the DSR infusate into a peritoneal cavity of the patient comprises transferring the DSR infusate into the peritoneal cavity of the patient from a reservoir using an implantable pump.

15. The method of claim 12, wherein the introducing the DSR infusate into a peritoneal cavity of the patient comprises infusing the DSR infusate into the peritoneal cavity of the patient using gravity to deliver the DSR infusate from a reservoir.

16. The method of claim 12, wherein the introducing the DSR infusate into a peritoneal cavity of the patient comprises delivering the DSR infusate using an extracorporeal pump, pressurized container or gravity-based feeding system.

17. The method of claim 12, wherein the removing the DSR infusate, sodium and osmotic ultrafiltrate from the peritoneal cavity of the patient comprises, upon expiration of the dwell period, transferring the DSR infusate, sodium and osmotic ultrafiltrate from the peritoneal cavity to a urinary bladder of the patient using an implantable pump.

18. The method of claim 17, further comprising activating the implantable pump at predetermined times to transfer a volume of the DSR infusate, sodium and osmotic ultrafiltrate from the peritoneal cavity to the urinary bladder of the patient.

19. The method of claim 12, further comprising, during the dwell period, monitoring an intra-abdominal pressure of the patient with one or more sensors.

20. The method of claim 19, further comprising, during the dwell period, monitoring the rate of fluid accumulation in the peritoneal cavity.

21. The method of claim 20, further comprising, during the dwell period, generating an alert to a physician indicative of the increase in the rate of fluid accumulation in the peritoneal cavity or increase in intra-abdominal pressure.

\* \* \* \* \*